US007195869B2

(12) United States Patent
Maekawa et al.

(10) Patent No.: US 7,195,869 B2
(45) Date of Patent: Mar. 27, 2007

(54) METHOD OF SEARCHING FOR GENE ENCODING NUCLEAR TRANSPORT PROTEIN

(75) Inventors: Takami Maekawa, Kawasaki (JP); Maiko Mori, Kawasaki (JP); Yoshiyuki Takahara, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 301 days.

(21) Appl. No.: 10/204,310

(22) PCT Filed: Nov. 6, 2001

(86) PCT No.: PCT/JP01/09700

§ 371 (c)(1),
(2), (4) Date: Aug. 21, 2002

(87) PCT Pub. No.: WO02/36823

PCT Pub. Date: May 10, 2002

(65) Prior Publication Data

US 2003/0180801 A1 Sep. 25, 2003

(30) Foreign Application Priority Data

Nov. 6, 2000 (JP) ............................ 2000-337906

(51) Int. Cl.
*C12Q 1/68* (2006.01)
*G01N 33/53* (2006.01)
*C12N 15/00* (2006.01)
*C07K 1/00* (2006.01)
*C07H 21/04* (2006.01)

(52) U.S. Cl. .......................... 435/6; 435/7.1; 435/91.2; 435/320.1; 530/350; 536/23.4

(58) Field of Classification Search .................... 435/6, 435/91.2; 536/23.1, 24.3
See application file for complete search history.

(56) References Cited

U.S. PATENT DOCUMENTS 5,891,924 A 4/1999 Aggarwal

FOREIGN PATENT DOCUMENTS

WO WO 00/17643 3/2000
WO WO 00/23615 4/2006

OTHER PUBLICATIONS

Sutherland, H.G.E. et al., "Large-scale identification of mammalian proteins localized to nuclear sub-compartments", Hum. Mol. Gen., vol. 10, pp. 1995-2011 (Sep. 2001).*

Tate, P. et al., "Capturing novel mouse genes encoding chromosomal and other nuclear proteins", J. Cell Sci., vol. 111, pp. 2575-2585 (1998).*

Sawin K. E. et al. "Identification of fission yeast nuclear markers using random polypeptide fusions with green fluorescent protein", PNAS, vol. 94, pp. 15146-15151 (1996).*

Rakowicz-Szulczynska, E.M., et al., "Nuclear uptake of monoclonal antibody to a surface glycoprotein and its efect on transcription", Arch. Biochem. Biophys., vol. 271(2), p. 366-79 (1989).*

Rakowicz-Szulczynska, E.M., et al., "intracellular receptor binding and nuclear transport of nerve growth factor in intact cells and a cell-free system", Mol. Carcinog., vol. 2, pp. 47-58 (1989).*

Gonzales, C. et al., "Protein traps: using intracellular localization for cloning", Trends in Cell Biol., vol. 10, pp. 162-165 (Apr. 2000).*

Turpin, P. et al., "Nuclear transport and transcriptional regulation", FEBS Letters, vol. 452, pp. 82-86 (1999).*

M.M. Rolls et al.: "A visual screen of a GFP-fusion library identifies of a new type of nuclear envelope membrane protein" J. Cell. Biol., vol. 146, No. 1, pp. 29-43 1999.

European Office Action dated Nov. 20, 2006, Issued I corresponding European patent Application No. 01979034.4.

A. Beg, et al., "IxB interacts With The Nuclear Localization Sequences of The Subunits of NF-xB: A Mechanism For Cytoplasmic Retention", Genes and Development, vol. 6, 1992, pp. 1889-1913.

* cited by examiner

*Primary Examiner*—Teresa E. Strzelecka
(74) *Attorney, Agent, or Firm*—Oblon, Spivak, McClelland, Maier & Neustadt, P.C.

(57) ABSTRACT

Each gene in a group comprising many genes is cloned into an expression vector so that its gene product should be expressed as a fusion protein with a protein emitting self-fluorescence to construct a gene expression library. The gene expression library is introduced into cells of two groups to express the fusion proteins in the cells, and only one cell group is stimulated by a drug or the like. Then, cells in which the fusion proteins are localized in the nuclei or their nuclei are isolated from cells of the two groups, respectively. By comparing these cells, genes coding for proteins that are transported into the nuclei specifically in response to a certain stimulus when the stimulus is applied to the cells are retrieved.

13 Claims, 4 Drawing Sheets

SEQUENCE LISTING

```
<160> NUMBER OF SEQ ID NOS: 19

<210> SEQ ID NO 1
<211> LENGTH: 6238
<212> TYPE: DNA
<213> ORGANISM: ARTIFICIAL SEQUENCE
<220> FEATURE:
<223> OTHER INFORMATION: SYNTHETIC DNA

<400> SEQUENCE: 1

gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcc tcgaggcctg gccattgcat acgttgtatc    240

catatcataa tatgtacatt tatattggct catgtccaac attaccgcca tgttgacatt    300

gattattgac tagttattaa tagtaatcaa ttacggggtc attagttcat agcccatata    360

tggagttccg cgttacataa cttacggtaa atggcccgcc tggctgaccg cccaacgacc    420

cccgcccatt gacgtcaata atgacgtatg ttcccatagt aacgccaata gggactttcc    480

attgacgtca atgggtggag tatttacggt aaactgccca cttggcagta catcaagtgt    540

atcatatgcc aagtacgccc cctattgacg tcaatgacgg taaatggccc gcctggcatt    600

atgcccagta catgacctta tgggactttc ctacttggca gtacatctac gtattagtca    660

tcgctattac catggtgatg cggttttggc agtacatcaa tgggcgtgga tagcggtttg    720

actcacgggg atttccaagt ctccacccca ttgacgtcaa tgggagtttg ttttggcacc    780

aaaatcaacg ggactttcca aaatgtcgta acaactccgc cccattgacg caaatgggcg    840

gtaggcgtgt acggtgggag gtctatataa gcagagctcg tttagtgaac cgtcagatcg    900

cctggagacg ccatccacgc tgttttgacc tccatagaag acaccgggac cgatccagcc    960

tccgcgggcg cgcaagaaat ggctagcaaa ggagaagaac tcttcactgg agttgtccca   1020

attcttgttg aattagatgg tgatgttaac ggccacaagt tctctgtcag tggagagggt   1080

gaaggtgatg caacatacgg aaaacttacc ctgaagttca tctgcactac tggcaaactg   1140
```

-continued

```
cctgttccat ggccaacact agtcactact ctgtgctatg gtgttcaatg cttttcaaga   1200
tacccggatc atatgaaacg gcatgacttt ttcaagagtg ccatgcccga aggttatgta   1260
caggaaagga ccatcttctt caaagatgac ggcaactaca agacacgtgc tgaagtcaag   1320
tttgaaggtg atacccttgt taatagaatc gagttaaaag gtattgactt caaggaagat   1380
ggcaacattc tgggacacaa attggaatac aactataact cacacaatgt atacatcatg   1440
gcagacaaac aaaagaatgg aatcaaagtg aacttcaaga cccgccacaa cattgaagat   1500
ggaagcgttc aactagcaga ccattatcaa caaaatactc caattggcga tggccctgtc   1560
cttttaccag acaaccatta cctgtccaca caatctgccc tttcgaaaga tcccaacgaa   1620
aagagagacc acatggtcct tcttgagttt gtaacagctg ctgggattac acatggcatg   1680
gatgaactgt acaactgagg atccactagt aacggccgcc agtgtgctgg aattctgcag   1740
atatccatca cactggcggc cgctcgagca tgcatctaga gggccctatt ctatagtgtc   1800
acctaaatgc tagagctcgc tgatcagcct cgactgtgcc ttctagttgc cagccatctg   1860
ttgtttgccc ctcccccgtg ccttccttga ccctggaagg tgccactccc actgtccttt   1920
cctaataaaa tgaggaaatt gcatcgcatt gtctgagtag gtgtcattct attctggggg   1980
gtggggtggg gcaggacagc aagggggagg attgggaaga caatagcagg catgctgggg   2040
atgcggtggg ctctatggct tctgaggcgg aaagaaccag ctggggctct agggggtatc   2100
cccacgcgcc ctgtagcggc gcattaagcg cggcgggtgt ggtggttacg cgcagcgtga   2160
ccgctacact tgccagcgcc ctagcgcccg ctcctttcgc tttcttccct tcctttctcg   2220
ccacgttcgc cggctttccc cgtcaagctc taaatcgggg catcccttta gggttccgat   2280
ttagtgcttt acggcacctc gaccccaaaa aacttgatta gggtgatggt tcacgtagtg   2340
ggccatcgcc ctgatagacg gtttttcgcc ctttgacgtt ggagtccacg ttctttaata   2400
gtggactctt gttccaaact ggaacaacac tcaaccctat ctcggtctat tcttttgatt   2460
tataagggat tttggggatt tcggcctatt ggttaaaaaa tgagctgatt taacaaaaat   2520
ttaacgcgaa ttaattctgt ggaatgtgtg tcagttaggg tgtggaaagt ccccaggctc   2580
cccaggcagg cagaagtatg caaagcatgc atctcaatta gtcagcaacc aggtgtggaa   2640
agtccccagg ctccccagca ggcagaagta tgcaaagcat gcatctcaat tagtcagcaa   2700
ccatagtccc gcccctaact ccgcccatcc cgcccctaac tccgcccagt tccgcccatt   2760
ctccgcccca tggctgacta attttttta tttatgcaga ggccgaggcc gcctctgcct   2820
ctgagctatt ccagaagtag tgaggaggct tttttggagg cctaggcttt tgcaaaaagc   2880
tcccgggagc ttgtatatcc attttcggat ctgatcaaga gacaggatga ggatcgtttc   2940
gcatgattga acaagatgga ttgcacgcag gttctccggc cgcttgggtg gagaggctat   3000
tcggctatga ctgggcacaa cagacaatcg gctgctctga tgccgccgtg ttccggctgt   3060
cagcgcaggg gcgcccggtt ctttttgtca agaccgacct gtccggtgcc ctgaatgaac   3120
tgcaggacga ggcagcgcgg ctatcgtggc tggccacgac gggcgttcct tgcgcagctg   3180
tgctcgacgt tgtcactgaa gcgggaaggg actggctgct attgggcgaa gtgccggggc   3240
aggatctcct gtcatctcac cttgctcctg ccgagaaagt atccatcatg gctgatgcaa   3300
tgcggcggct gcatacgctt gatccggcta cctgcccatt cgaccaccaa gcgaaacatc   3360
gcatcgagcg agcacgtact cggatggaag ccggtcttgt cgatcaggat gatctggacg   3420
aagagcatca ggggctcgcg ccagccgaac tgttcgccag gctcaaggcg cgcatgcccg   3480
acggcgagga tctcgtcgtg acccatggcg atgcctgctt gccgaatatc atggtggaaa   3540
```

-continued

```
atggccgctt ttctggattc atcgactgtg gccggctggg tgtggcggac cgctatcagg   3600
acatagcgtt ggctacccgt gatattgctg aagagcttgg cggcgaatgg gctgaccgct   3660
tcctcgtgct ttacggtatc gccgctcccg attcgcagcg catcgccttc tatcgccttc   3720
ttgacgagtt cttctgagcg ggactctggg gttcgaaatg accgaccaag cgacgcccaa   3780
cctgccatca cgagatttcg attccaccgc cgccttctat gaaaggttgg gcttcggaat   3840
cgttttccgg gacgccggct ggatgatcct ccagcgcggg gatctcatgc tggagttctt   3900
cgcccacccc aacttgttta ttgcagctta taatggttac aaataaagca atagcatcac   3960
aaatttcaca aataaagcat ttttttcact gcattctagt tgtggtttgt ccaaactcat   4020
caatgtatct tatcatgtct gtataccgtc gacctctagc tagagcttgg cgtaatcatg   4080
gtcatagctg tttcctgtgt gaaattgtta tccgctcaca attccacaca acatacgagc   4140
cggaagcata aagtgtaaag cctggggtgc ctaatgagtg agctaactca cattaattgc   4200
gttgcgctca ctgcccgctt tccagtcggg aaacctgtcg tgccagctgc attaatgaat   4260
cggccaacgc gcggggagag gcggtttgcg tattgggcgc tcttccgctt cctcgctcac   4320
tgactcgctg cgctcggtcg ttcggctgcg gcgagcggta tcagctcact caaaggcggt   4380
aatacggtta tccacagaat caggggataa cgcaggaaag aacatgtgag caaaaggcca   4440
gcaaaaggcc aggaaccgta aaaaggccgc gttgctggcg tttttccata ggctccgccc   4500
ccctgacgag catcacaaaa atcgacgctc aagtcagagg tggcgaaacc cgacaggact   4560
ataaagatac caggcgtttc cccctggaag ctccctcgtg cgctctcctg ttccgaccct   4620
gccgcttacc ggatacctgt ccgcctttct cccttcggga agcgtggcgc tttctcaatg   4680
ctcacgctgt aggtatctca gttcggtgta ggtcgttcgc tccaagctgg gctgtgtgca   4740
cgaacccccc gttcagcccg accgctgcgc cttatccggt aactatcgtc ttgagtccaa   4800
cccggtaaga cacgacttat cgccactggc agcagccact ggtaacagga ttagcagagc   4860
gaggtatgta ggcggtgcta cagagttctt gaagtggtgg cctaactacg gctacactag   4920
aaggacagta tttggtatct gcgctctgct gaagccagtt accttcggaa aaagagttgg   4980
tagctcttga tccggcaaac aaaccaccgc tggtagcggt ggtttttttg tttgcaagca   5040
gcagattacg cgcagaaaaa aaggatctca agaagatcct ttgatctttt ctacggggtc   5100
tgacgctcag tggaacgaaa actcacgtta agggattttg gtcatgagat tatcaaaaag   5160
gatcttcacc tagatccttt taaattaaaa atgaagtttt aaatcaatct aaagtatata   5220
tgagtaaact tggtctgaca gttaccaatg cttaatcagt gaggcaccta tctcagcgat   5280
ctgtctattt cgttcatcca tagttgcctg actccccgtc gtgtagataa ctacgatacg   5340
ggagggctta ccatctggcc ccagtgctgc aatgataccg cgagacccac gctcaccggc   5400
tccagattta tcagcaataa accagccagc cggaagggcc gagcgcagaa gtggtcctgc   5460
aactttatcc gcctccatcc agtctattaa ttgttgccgg gaagctagag taagtagttc   5520
gccagttaat agtttgcgca acgttgttgc cattgctaca ggcatcgtgg tgtcacgctc   5580
gtcgtttggt atggcttcat tcagctccgg ttcccaacga tcaaggcgag ttacatgatc   5640
ccccatgttg tgcaaaaaag cggttagctc cttcggtcct ccgatcgttg tcagaagtaa   5700
gttggccgca gtgttatcac tcatggttat ggcagcactg cataattctc ttactgtcat   5760
gccatccgta agatgctttt ctgtgactgg tgagtactca accaagtcat tctgagaata   5820
gtgtatgcgg cgaccgagtt gctcttgccc ggcgtcaata cgggataata ccgcgccaca   5880
```

-continued tagcagaact ttaaaagtgc tcatcattgg aaaacgttct tcggggcgaa aactctcaag 5940
gatcttaccg ctgttgagat ccagttcgat gtaacccact cgtgcaccca actgatcttc 6000
agcatctttt actttcacca gcgtttctgg gtgagcaaaa acaggaaggc aaaatgccgc 6060
aaaaaaggga ataagggcga cacggaaatg ttgaatactc atactcttcc tttttcaata 6120
ttattgaagc atttatcagg gttattgtct catgagcgga tacatatttg aatgtattta 6180
gaaaaataaa caaatagggg ttccgcgcac atttccccga aaagtgccac ctgacgtc 6238

<210> SEQ ID NO 2
<211> LENGTH: 39
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
tgttggccat ggaacaggca gtttgccagt agtacagat 39

<210> SEQ ID NO 3
<211> LENGTH: 17
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
ggtaggcgtg tacggtg 17

<210> SEQ ID NO 4
<211> LENGTH: 36
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
gtgcagatct gattgaatga tatcggatcc tctaga 36

<210> SEQ ID NO 5
<211> LENGTH: 37
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
agtgcagatc tgattgaatg atatcggatc ctctaga 37

<210> SEQ ID NO 6
<211> LENGTH: 38
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
aagtgcagat ctgattgaat gatatcggat cctctaga 38

<210> SEQ ID NO 7
<211> LENGTH: 55
<212> TYPE: DNA
<213> ORGANISM: ARTIFICIAL SEQUENCE
<220> FEATURE:
<223> OTHER INFORMATION: SYNTHETIC DNA

-continued

<400> SEQUENCE: 7
gctctagagg atccgatatc attcaatcag atctgcacgt tgtacagttc atcca 55

<210> SEQ ID NO 8
<211> LENGTH: 56
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
gctctagagg atccgatatc attcaatcag atctgcactg ttgtacagtt catcca 56

<210> SEQ ID NO 9
<211> LENGTH: 57
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
gctctagagg atccgatatc attcaatcag atctgcactt gttgtacagt tcatcca 57

<210> SEQ ID NO 10
<211> LENGTH: 6195
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
gacggatcgg gagatcgatc tcccgatccc ctatggtcga ctctcagtac aatctgctct 60
gatgccgcat agttaagcca gtatctgctc cctgcttgtg tgttggaggt cgctgagtag 120
tgcgcgagca aaatttaagc tacaacaagg caaggcttga ccgacaattg catgaagaat 180
ctgcttaggg ttaggcgttt tgcgctgctt cgcctcgagg cctggccatt gcatacgttg 240
tatccatatc ataatatgta catttatatt ggctcatgtc caacattacc gccatgttga 300
cattgattat tgactagtta ttaatagtaa tcaattacgg ggtcattagt tcatagccca 360
tatatggagt tccgcgttac ataacttacg gtaaatggcc cgcctggctg accgcccaac 420
gacccccgcc cattgacgtc aataatgacg tatgttccca tagtaacgcc aatagggact 480
ttccattgac gtcaatgggt ggagtattta cggtaaactg cccacttggc agtacatcaa 540
gtgtatcata tgccaagtac gccccctatt gacgtcaatg acggtaaatg gcccgcctgg 600
cattatgccc agtacatgac cttatgggac tttcctactt ggcagtacat ctacgtatta 660
gtcatcgcta ttaccatggt gatgcggttt tggcagtaca tcaatgggcg tggatagcgg 720
tttgactcac ggggatttcc aagtctccac cccattgacg tcaatgggag tttgttttgg 780
caccaaaatc aacgggactt tccaaaatgt cgtaacaact ccgccccatt gacgcaaatg 840
ggcggtaggc gtgtacggtg ggaggtctat ataagcagag ctcgtttagt gaaccgtcag 900
atcgcctgga gacgccatcc acgctgtttt gacctccata gaagacaccg ggaccgatcc 960
agcctccgcg ggcgcgcaag aaatggctag caaaggagaa gaactcttca ctggagttgt 1020
cccaattctt gttgaattag atggtgatgt taacggccac aagttctctg tcagtggaga 1080
gggtgaaggt gatgcaacat acggaaaact taccctgaag ttcatctgta ctactggcaa 1140
actgcctgtt ccatggccaa cactagtcac tactctgtgc tatggtgttc aatgcttttc 1200

-continued

```
aagatacccg gatcatatga aacggcatga ctttttcaag agtgccatgc ccgaaggtta   1260
tgtacaggaa aggaccatct tcttcaaaga tgacggcaac tacaagacac gtgctgaagt   1320
caagtttgaa ggtgataccc ttgttaatag aatcgagtta aaaggtattg acttcaagga   1380
agatggcaac attctgggac acaaattgga atacaactat aactcacaca atgtatacat   1440
catggcagac aaacaaaaga atggaatcaa agtgaacttc aagacccgcc acaacattga   1500
agatggaagc gttcaactag cagaccatta tcaacaaaat actccaattg gcgatggccc   1560
tgtcctttta ccagacaacc attacctgtc cacacaatct gccctttcga aagatcccaa   1620
cgaaaagaga gaccacatgg tccttcttga gtttgtaaca gctgctggga ttacacatgg   1680
catggatgaa ctgtacaaca agtgcagatc tgattgaatg atatcggatc ctctagaggg   1740
ccctattcta tagtgtcacc taaatgctag agctcgctga tcagcctcga ctgtgccttc   1800
tagttgccag ccatctgttg tttgcccctc ccccgtgcct tccttgaccc tggaaggtgc   1860
cactcccact gtcctttcct aataaaatga ggaaattgca tcgcattgtc tgagtaggtg   1920
tcattctatt ctggggggtg gggtggggca ggacagcaag ggggaggatt gggaagacaa   1980
tagcaggcat gctggggatg cggtgggctc tatggcttct gaggcggaaa gaaccagctg   2040
gggctctagg gggtatcccc acgcgccctg tagcggcgca ttaagcgcgg cgggtgtggt   2100
ggttacgcgc agcgtgaccg ctacacttgc cagcgcccta gcgcccgctc ctttcgcttt   2160
cttcccttcc tttctcgcca cgttcgccgg ctttccccgt caagctctaa atcggggcat   2220
ccctttaggg ttccgattta gtgctttacg gcacctcgac cccaaaaaac ttgattaggg   2280
tgatggttca cgtagtgggc catcgccctg atagacggtt tttcgccctt tgacgttgga   2340
gtccacgttc tttaatagtg gactcttgtt ccaaactgga acaacactca accctatctc   2400
ggtctattct tttgatttat aagggatttt ggggatttcg gcctattggt taaaaaatga   2460
gctgatttaa caaaaattta acgcgaatta attctgtgga atgtgtgtca gttagggtgt   2520
ggaaagtccc caggctcccc aggcaggcag aagtatgcaa agcatgcatc tcaattagtc   2580
agcaaccagg tgtggaaagt ccccaggctc cccagcaggc agaagtatgc aaagcatgca   2640
tctcaattag tcagcaacca tagtcccgcc cctaactccg cccatcccgc ccctaactcc   2700
gcccagttcc gcccattctc cgccccatgg ctgactaatt ttttttattt atgcagaggc   2760
cgaggccgcc tctgcctctg agctattcca gaagtagtga ggaggctttt ttggaggcct   2820
aggcttttgc aaaaagctcc cgggagcttg tatatccatt ttcggatctg atcaagagac   2880
aggatgagga tcgtttcgca tgattgaaca agatggattg cacgcaggtt ctccggccgc   2940
ttgggtggag aggctattcg gctatgactg ggcacaacag acaatcggct gctctgatgc   3000
cgccgtgttc cggctgtcag cgcaggggcg cccggttctt tttgtcaaga ccgacctgtc   3060
cggtgccctg aatgaactgc aggacgaggc agcgcggcta tcgtggctgg ccacgacggg   3120
cgttccttgc gcagctgtgc tcgacgttgt cactgaagcg ggaagggact ggctgctatt   3180
gggcgaagtg ccggggcagg atctcctgtc atctcacctt gctcctgccg agaaagtatc   3240
catcatggct gatgcaatgc ggcggctgca tacgcttgat ccggctacct gcccattcga   3300
ccaccaagcg aaacatcgca tcgagcgagc acgtactcgg atggaagccg gtcttgtcga   3360
tcaggatgat ctggacgaag agcatcaggg gctcgcgcca gccgaactgt tcgccaggct   3420
caaggcgcgc atgcccgacg gcgaggatct cgtcgtgacc catggcgatg cctgcttgcc   3480
gaatatcatg gtggaaaatg gccgcttttc tggattcatc gactgtggcc ggctgggtgt   3540
ggcggaccgc tatcaggaca tagcgttggc tacccgtgat attgctgaag agcttggcgg   3600
```

-continued

```
cgaatgggct gaccgcttcc tcgtgcttta cggtatcgcc gctcccgatt cgcagcgcat   3660
cgccttctat cgccttcttg acgagttctt ctgagcggga ctctggggtt cgaaatgacc   3720
gaccaagcga cgcccaacct gccatcacga gatttcgatt ccaccgccgc cttctatgaa   3780
aggttgggct tcggaatcgt tttccgggac gccggctgga tgatcctcca gcgcggggat   3840
ctcatgctgg agttcttcgc ccaccccaac ttgtttattg cagcttataa tggttacaaa   3900
taaagcaata gcatcacaaa tttcacaaat aaagcatttt tttcactgca ttctagttgt   3960
ggtttgtcca aactcatcaa tgtatcttat catgtctgta taccgtcgac ctctagctag   4020
agcttggcgt aatcatggtc atagctgttt cctgtgtgaa attgttatcc gctcacaatt   4080
ccacacaaca tacgagccgg aagcataaag tgtaaagcct ggggtgccta atgagtgagc   4140
taactcacat taattgcgtt gcgctcactg cccgctttcc agtcgggaaa cctgtcgtgc   4200
cagctgcatt aatgaatcgg ccaacgcgcg gggagaggcg gtttgcgtat tgggcgctct   4260
tccgcttcct cgctcactga ctcgctgcgc tcggtcgttc ggctgcggcg agcggtatca   4320
gctcactcaa aggcggtaat acggttatcc acagaatcag gggataacgc aggaaagaac   4380
atgtgagcaa aaggccagca aaaggccagg aaccgtaaaa aggccgcgtt gctggcgttt   4440
ttccataggc tccgcccccc tgacgagcat cacaaaaatc gacgctcaag tcagaggtgg   4500
cgaaacccga caggactata aagataccag gcgtttcccc ctggaagctc cctcgtgcgc   4560
tctcctgttc cgaccctgcc gcttaccgga tacctgtccg cctttctccc ttcgggaagc   4620
gtggcgcttt ctcaatgctc acgctgtagg tatctcagtt cggtgtaggt cgttcgctcc   4680
aagctgggct gtgtgcacga accccccgtt cagcccgacc gctgcgcctt atccggtaac   4740
tatcgtcttg agtccaaccc ggtaagacac gacttatcgc cactggcagc agccactggt   4800
aacaggatta gcagagcgag gtatgtaggc ggtgctacag agttcttgaa gtggtggcct   4860
aactacggct acactagaag gacagtattt ggtatctgcg ctctgctgaa gccagttacc   4920
ttcggaaaaa gagttggtag ctcttgatcc ggcaaacaaa ccaccgctgg tagcggtggt   4980
ttttttgttt gcaagcagca gattacgcgc agaaaaaaag gatctcaaga agatcctttg   5040
atcttttcta cggggtctga cgctcagtgg aacgaaaact cacgttaagg gattttggtc   5100
atgagattat caaaaaggat cttcacctag atccttttaa attaaaaatg aagttttaaa   5160
tcaatctaaa gtatatatga gtaaacttgg tctgacagtt accaatgctt aatcagtgag   5220
gcacctatct cagcgatctg tctatttcgt tcatccatag ttgcctgact ccccgtcgtg   5280
tagataacta cgatacggga gggcttacca tctggcccca gtgctgcaat gataccgcga   5340
gacccacgct caccggctcc agatttatca gcaataaacc agccagccgg aagggccgag   5400
cgcagaagtg gtcctgcaac tttatccgcc tccatccagt ctattaattg ttgccgggaa   5460
gctagagtaa gtagttcgcc agttaatagt ttgcgcaacg ttgttgccat tgctacaggc   5520
atcgtggtgt cacgctcgtc gtttggtatg gcttcattca gctccggttc ccaacgatca   5580
aggcgagtta catgatcccc catgttgtgc aaaaaagcgg ttagctcctt cggtcctccg   5640
atcgttgtca gaagtaagtt ggccgcagtg ttatcactca tggttatggc agcactgcat   5700
aattctctta ctgtcatgcc atccgtaaga tgcttttctg tgactggtga gtactcaacc   5760
aagtcattct gagaatagtg tatgcggcga ccgagttgct cttgcccggc gtcaatacgg   5820
gataataccg cgccacatag cagaacttta aaagtgctca tcattggaaa acgttcttcg   5880
gggcgaaaac tctcaaggat cttaccgctg ttgagatcca gttcgatgta acccactcgt   5940
```

-continued

```
gcacccaact gatcttcagc atcttttact ttcaccagcg tttctgggtg agcaaaaaca   6000

ggaaggcaaa atgccgcaaa aaagggaata agggcgacac ggaaatgttg aatactcata   6060

ctcttccttt ttcaatatta ttgaagcatt tatcagggtt attgtctcat gagcggatac   6120

atatttgaat gtatttagaa aaataaacaa ataggggttc cgcgcacatt tccccgaaaa   6180

gtgccacctg acgtc                                                     6195


<210> SEQ ID NO 11
<211> LENGTH: 32
<212> TYPE: DNA
<213> ORGANISM: ARTIFICIAL SEQUENCE
<220> FEATURE:
<223> OTHER INFORMATION: SYNTHETIC DNA

<400> SEQUENCE: 11

cagagcagat cttgagatgc ggctgcagaa cg                                    32


<210> SEQ ID NO 12
<211> LENGTH: 34
<212> TYPE: DNA
<213> ORGANISM: ARTIFICIAL SEQUENCE
<220> FEATURE:
<223> OTHER INFORMATION: SYNTHETIC DNA[ ]

<400> SEQUENCE: 12

cagcatctag aacacaggtg gggccactca ctgg                                  34


<210> SEQ ID NO 13
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 13

aagagagacc acatggtcct                                                  20


<210> SEQ ID NO 14
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 14

ccagaataga atgacaccta ctc                                              23


<210> SEQ ID NO 15
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 15

gccttccact catcttcagc ctt                                              23


<210> SEQ ID NO 16
<211> LENGTH: 38
<212> TYPE: DNA
<213> ORGANISM: ARTIFICIAL SEQUENCE
<220> FEATURE:
<223> OTHER INFORMATION: SYNTHETIC DNA

<400> SEQUENCE: 16
```

-continued

```
aagcttggta ccgagctcgg atccactatt ccagtgtg                          38


<210> SEQ ID NO 17
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 17

aactagaagg cacagtcgag gctgatca                                     28


<210> SEQ ID NO 18
<211> LENGTH: 16
<212> TYPE: DNA
<213> ORGANISM: ARTIFICIAL SEQUENCE
<220> FEATURE:
<223> OTHER INFORMATION: SYNTHETIC DNA

<400> SEQUENCE: 18

aggcacagtc gaggct                                                  16


<210> SEQ ID NO 19
<211> LENGTH: 9
<212> TYPE: PRT
<213> ORGANISM: Influenza virus

<400> SEQUENCE: 19

Tyr Pro Tyr Asp Val Pro Asp Tyr Ala
1               5
```

METHOD OF SEARCHING FOR GENE ENCODING NUCLEAR TRANSPORT PROTEIN

TECHNICAL FIELD

The present invention relates to a method for searching for a gene coding for a protein that is transported from cytoplasm of a eukaryotic cell into a nucleus through a nuclear pore. More precisely, the present invention relates to a method for efficiently searching for a gene coding for a protein that is specifically transported from cytoplasm of a eukaryotic cell into a nucleus in response to a certain stimulus. Further, the present invention also relates to a method for screening a therapeutic agent for a disease caused by TNF stimulus by utilizing a protein which is transported from cytoplasm of a eukaryotic cell into a nucleus through a nuclear pore or a gene coding for the same.

BACKGROUND ART

Cells receive various stimuli from the outside and react in response to these stimuli. Examples of such stimuli include binding of cytokine or hormone to a receptor, viral infection, physical contact with other cells, thermal stimuli such as high or low temperature, pH, drug stimulus, stimulus from a substance such as nutrients and amino acids in the environment surrounding the cells and so forth. In many cases, when a cell reacts in response to such a stimulus, the stimulus is transmitted to the nucleus as a signal, and as a result, expression of a certain gene is regulated. As in the case of lipid-soluble hormones, some proteins pass through a cell membrane and nuclear membrane and directly bind to a receptor in the nucleus to regulate transcription. However, many signals are first captured on the cell membrane, and then a stimulus is passed onto signal transducing molecules and transmitted from the cytoplasm to the nucleus by the signal transducing molecules. Transport of some of these transducing molecules from the cytoplasm into the nucleus is known to be essential to the signal transduction. Several signal transducing molecules, which pass through a nuclear membrane, such as STAT1 (Science, 277: p.1630–1635 (1997)) and NFκB (Annu. Rev. Immunol., 16: p.225–260 (1998)), have been identified to date, but it is considered that there are still many unknown molecules.

A large number of proteins that are simply transported from the cytoplasm into the nucleus have been found by various research methods. Proteins constituting the nucleus or so-called nucleoproteins identified to date are synthesized as a peptide from mRNA in the cytoplasm and then transported into the nucleus. These proteins can also be regarded as proteins that are transported into the nucleus. Examples of the nucleus constituting proteins include nucleohistone, nucleoprotamine, lamin and so forth. However, many of these are not considered directly involved in the signal transduction.

As a method for searching for and identifying, not proteins that are constantly localized in the nucleus as described above, but proteins that are transported to the nucleus, there is an example in which a gene coding for a GFP protein, which emits self-fluorescence, was ligated with cDNA to express a fusion protein, so that a protein having a nuclear transport signal encoded by the cDNA portion was isolated by using fluorescence emitted by the GFP as a marker (The Journal of Cell Biology, 146, 29–43, 1999). However, with this method, proteins having a nuclear transport signal are only identified, and cDNA of proteins such as so-called signal transducing molecules, which are transported from the cytoplasm into the nucleus in response to a certain stimulus, cannot be isolated.

Meanwhile, TNF is released mainly from immune system cells upon inflammation and induces inflammation as a biophylactic reaction. However, when this action becomes excessive, various diseases are developed. For example, when hepatitis, which is caused by viral infection, is developed into chronic state, chronic production of TNF induces fibrosis of the liver, and progression of this condition causes cirrhosis. It is also known that inflammation is relieved by TNF antibodies in many diseases such as hepatitis, enteritis, pneumonia, nephritis and arthritis. In fact, commercially available anti-TNF antibodies show remarkable effects as therapeutic agents.

Furthermore, TNF is involved in the biophylactic reactions and plays an important role in activation of immunocompetent cells, repair of organs and elimination of tumors. In treatment of diseases associated with TNF, it is considered to be effective that TNF actions should not be totally suppressed, but that only a harmful part of the TNF actions should be suppressed or only a useful part should be enhanced.

TNF actions vary depending on the kind of the cell or the state of the cell, and TNF exhibits various actions. For example, in a liver cell, TNF binds to a TNF receptor and induces both a signal inducing apoptosis (death signal) and a signal inducing expression of various genes (gene expression inducing signal) via a transcription factor such as NFκB. The former signal is not accompanied by induction of gene expression. The latter signal induces gene expression, and a part of proteins produced thereby has an action for canceling the death signal (anti-apoptosis action). Usually, these two types of signals are balanced, and a normal cell exposed to TNF does not undergo apoptosis. When the anti-apoptosis action is inhibited due to some cause, a cell undergoes apoptosis. For example, fulminant hepatitis is a disease wherein a wide range of liver cells rapidly undergo apoptosis. Its mortality is extremely high, and no good therapy is available. It is considered that this is resulted from failure of the anti-apoptosis mechanism of the liver cells against TNF due to some cause and induction of only apoptosis signals by TNF.

Thus, various actions of TNF are considered to be attributable to actions of various transcription factors that transmit TNF signals.

A gene expression promoting signal induced by TNF induces gene expressions by a mechanism in which a certain protein receiving the signal from a TNF receptor is transported from the cytoplasm into the nucleus to form a certain complex and bind to a transcription regulating region so that the gene expression should be induced. The expressed genes show various aspects depending on the kind of the cell and influences of other signals that simultaneously exist. It is considered that each protein which is transported into the nucleus plays a different role and is involved in a different gene expression.

As the nuclear transport molecule that transmits TNF signals, NFκB is known. NFκB is a nuclear transport protein that leads presence of, not only TNF, but also many cytokines, growth factors and stress stimulus, to gene expressions. Considering diversity of the TNF actions, it seems impossible that NFκB should be the only transcription factor of TNF. Therefore, it is expected that there exist unknown proteins that are transported into the nucleus in response to TNF stimulus.

Disclosure of the Invention

An object of the present invention is to provide a method for searching for a gene coding for a protein that is specifically transported into a nucleus in response to a certain stimulus applied to a cell. Further, another object of the present invention is to provide a method for screening a therapeutic agent for a diseases caused by TNF stimulus by utilizing a protein which is transported from cytoplasm of a eukaryotic cell into a nucleus through a nuclear pore or a gene coding for the same.

The inventors of the present invention assiduously studied in order to achieve the above objects. As a result, they found that an object gene could be retrieved by cloning each gene in many gene groups into an expression vector so that its gene product should be expressed as a fusion protein with a protein emitting self-fluorescence to construct a gene expression library, introducing this gene expression library into two groups of cells so that the fusion proteins should be expressed in the cells, stimulating only one cell group by a drug or the like, isolating cells in which the fusion proteins were localized in the nuclei or the nuclei thereof from the cells of the two groups, respectively, and then comparing them. Thus, they accomplished the present invention.

That is, the following are provided by the present invention.

(1) A method for searching for a gene coding for a protein which is transported from cytoplasm into a nucleus through a nuclear pore in a eukaryotic cell, comprising the steps of:

(a) introducing a library of genes coding for fusion proteins of a marker protein whose localization in a cell can be detected and a part or whole of a search object protein into eukaryotic cells to allow expression of the genes in the transgenic cells so that the fusion proteins should be produced;

(b) dividing the transgenic cells into two groups and stimulating only cells of one group so that a nuclear transport protein should be transported into nuclei;

(c) detecting localization of the fusion proteins in cells by using the marker protein in each of the stimulated cell group and the unstimulated cell group and isolating cells in which the fusion proteins are localized in the nuclei or their nuclei; and (d) recovering genes coding for a fusion protein from the isolated cells or their nuclei, and comparing genes recovered from the stimulated cell group and genes recovered from the unstimulated cell group.

(2) The method according to (1), which comprises, after the step (d), a step of identifying a gene recovered only from the stimulated cell group or a gene recovered only from the unstimulated cell group.

(3) The method according to (1) or (2), wherein, in the step (c), operations of detecting localization of the fusion proteins in a cell based on the marker protein and isolating cells or nuclei in which localization of the fusion proteins is observed in the nuclei are repeated twice or more for the isolated cells or nuclei.

(4) The method according to any one of (1) to (3), wherein the marker protein is a protein emitting self-fluorescence, a protein catalyzing color development reaction, an antigen peptide that can be detected with an antibody or a peptide that can bind to another substance.

(5) The method according to (4), wherein the protein emitting self-fluorescence is a green fluorescent protein.

(6) The method according to any one of (1) to (5), wherein, in the step (b), the transport of the nuclear transport protein into the nuclei is stimulated by means selected from the group consisting of a chemical substance, a physiologically active substance, environmental change and contact with other cells.

(7) The method according to any one of (1) to (6), wherein the cells or their nuclei are isolated by cell sorting, flow cytometry, microdissection or microscopic observation.

(8) The method according to any one of (1) to (7), wherein, in the step (c), permeability of the cell membranes is increased so that the fusion proteins in the cytoplasm should be flown out of the cells prior to the isolation of the cells.

(9) The method according to any one of (1) to (8), wherein, in the step (c), the cell membranes of the cells are disrupted and then the nuclei are isolated.

(10) The method according to any one of (1) to (9), wherein, in the step (d), the genes recovered from the stimulated cell group and the genes recovered from the unstimulated cell group are compared based on sequence analysis of full length or a part of a region coding for a search object protein for the genes.

(11) The method according to any one of (1) to (10), wherein, in the step (a), one or more genes coding for a fusion protein autonomously transporting into the nucleus with no stimulus are eliminated from the gene library beforehand.

(12) The method according to any one of (1) to (11), wherein, in the step (a), one or more genes coding for a fusion protein with an extranuclear protein, which is never transported into the nucleus, are eliminated from the gene library beforehand.

(13) The method according to any one of (1) to (12), wherein, in the step (a), the search object protein is a protein which regulates gene transcription.

(14) The method according to any one of (1) to (13), wherein, in the step (a), the fusion proteins further include a nuclear export signal.

(15) A method for screening a therapeutic agent for a disease caused by TNF stimulus, comprising the steps of:

(a) preparing eukaryotic cells expressing a protein which is transported from cytoplasm into a nucleus through a nuclear pore in response to TNF stimulus;

(b) allowing TNF and a test substance to act on the eukaryotic cells;

(c) detecting a protein transported into the nucleus; and (d) selecting a test substance that accelerates or inhibits the nuclear transport of the protein when the test substance is allowed to act on the cells in comparison to a case where the test substance is not allowed to act on the cells.

(16) The method according to (15), wherein the eukaryotic cells express the protein which is transported into a nucleus because of introduction of a gene coding for the protein.

(17) The method according to (16), wherein the protein which is transported into a nucleus is a fusion protein with a marker protein whose localization in a cell can be detected.

(18) The method according to any one of (15) to (17), wherein the eukaryotic cells are transformant cells transformed with a foreign gene other than the gene coding for the protein, and an expression product of the foreign gene is the test substance.

(19) The method according to (18), wherein the eukaryotic cells are transformants introduced with a gene library.

(20) The method according to any one of (15) to (19), wherein the protein which is transported into a nucleus is a product of a gene selected from human genes of UniGene numbers Hs.12303, Hs.183180, Hs.198246, Hs.83849, Hs.76722, Hs.74034, Hs.129959, Hs.24301, Hs.24756, Hs.161137, Hs.348609 and Hs.24608.

Hereafter, the present invention will be explained in detail.

<1> Method for Screening Nuclear Transport Protein of the Present Invention

The first aspect of the present invention relates to a method for searching for a gene coding for a protein transported from cytoplasm of a eukaryotic cell into a nucleus through a nuclear pore. In the present invention, when transport of a protein from cytoplasm of a eukaryotic cell into a nucleus through a nuclear pore is referred to as "nuclear transport". The protein which is transported into the nucleus is referred to as a "nuclear transport protein". In the present invention, specifically, the nuclear transport protein is a protein that is transported into a nucleus when a cell is stimulated by a certain stimulus.

The method of the present invention comprises the following steps:

(a) introducing a library of genes coding for fusion proteins of a marker protein whose localization in a cell can be detected and a part or whole of a search object protein into eukaryotic cells to allow expression of the genes in transgenic cells so that the fusion proteins should be produced;

(b) dividing the transgenic cells into two groups and stimulating only cells of one group so that a nuclear transport protein should be transported into nuclei;

(c) detecting localization of the fusion proteins in cells by using the marker protein in each of the stimulated cell group and the unstimulated cell group and isolating cells in which the fusion proteins are localized in the nucleus or their nuclei; and (d) recovering genes coding for a fusion protein from the isolated cells or their nuclei, and comparing genes recovered from the stimulated cell group and genes recovered from the unstimulated cell group.

Hereafter, the method of the present invention will be explained step by step.

(1) Step (a)

First, a gene library of genes coding for fusion proteins of a marker protein whose localization in a cell can be detected and a part or whole of a search object protein is constructed. The marker protein can be used to detect localization of the fusion proteins in a cell by detecting the marker protein itself, and is not particularly limited so long as it dose not substantially inhibit nuclear transport of the fusion proteins. As for the detection of the localization in a cell, the localization can be preferably visualized while substantially maintaining the cellular or nuclear structure. The marker protein may be one that can be detected directly or indirectly by a visual or electrical method or the like. Specific examples of the marker protein include a protein emitting self-fluorescence, protein catalyzing a color development reaction, antigen peptide that can be detected by an antibody or peptide that can specifically bind to anther substance.

As the protein emitting self-fluorescence, there can be mentioned, for example, a green fluorescent protein (GFP). The self-fluorescence used herein refers to light emitted by absorbing energy from outside such as excitation light, and its fluorescence wavelength is not particularly limited so long as it can be detected. Phosphorescence is also included. GFP is a protein recently found in Aequorea (Proc. Natl. Acad. Sci. USA, 91: 12501–12504 (1994)), and does not require a cofactor such as a metal ion for light emission unlike chlorophyll or the like. Therefore, GFP is suitable to find localization in a cell. Nuclei containing GFP can be isolated, for example, by sorting with a flow cytometer. Further, the position of nuclei can be confirmed by staining using Hoechst 33342 (Molecular Probes, Inc.) and the amount of GFP in the recognized nuclei can be quantified by using an ArrayScan system (Cellomics).

As the protein catalyzing a color development reaction, there can be mentioned alkaline phosphatase, peroxidase, β-galactosidase and so forth. The antigen peptide that can be detected by using an antibody is not particularly limited so long as it has antigenicity and its localization can be detected based on an antigenantibody reaction. Specifically, there can be mentioned a histidine polymer (His tag), a peptide sequence YPYDVPDYA (SEQ ID NO: 19, HA tag) contained in the hemagglutinin protein of influenza virus, a peptide of which N-terminus or C-terminus is bonded to either one of these and so forth.

Examples of the peptide that can specifically bind to another substance include avidin or streptavidin, which specifically binds to biotin, or protein A which specifically binds to an immunoglobulin, and so forth.

A method for constructing a gene library of genes coding for fusion proteins of a marker protein and a part or whole of a search object protein as described above will be explained below.

The gene library utilizes a vector DNA suitable to transiently express a fusion protein in a cell as a basic structure. As the vector, a plasmid vector or viral vector is usually used. Preferably, a so-called expression vector is used, which includes an expression regulatory sequence such as a promoter that enables expression in a eukaryotic cell.

A gene coding for a fusion protein is obtained by ligating DNA coding for a marker protein (marker protein gene) and DNA coding for a search object protein (object gene). The manner of fusion of the marker protein and the search object protein is not particularly limited, but it is usually preferable to position the marker protein on the N-terminal side and the search object protein on the C-terminal side. A termination codon is eliminated from the marker protein gene beforehand so that translation of the fusion protein should not be terminated. Further, DNA coding for a polypeptide such as a linker may be disposed between the marker protein gene and the object gene, but, in this case, an in-frame termination codon needs to be prevented from existing.

The fusion protein gene is inserted into a vector DNA in such a manner that a gene coding for the fusion protein can be expressed. Concrete procedures for constructing a fusion gene library will be exemplified below.

First, in order to prepare a cloning vector for cloning an object gene, a marker protein gene is inserted into a multicloning site located immediately downstream from a promoter in an expression vector. At this time, a cloning site for insertion of the object gene is provided downstream from the marker protein gene. Subsequently, the object gene is inserted into a cloning site of the cloning vector. As the object gene, cDNA is typically used. As the cDNA, double-stranded DNA is used, which is obtained from a single-stranded cDNA synthesized by reverse transcription using mRNA prepared from a cell or tissue as a template. The cDNA may include the whole or a part of a coding region. Since mRNA prepared from a cell or tissue is a mixture of those transcribed from many kinds of genes, a library including many kinds of genes is constructed by using such mRNA as a starting material for constructing the library. It is preferred that as many kinds as possible of cDNA are cloned in the library, but vector DNA and cDNA are preferably ligated so that one arbitrary kind of cDNA should be inserted into the cloning vector.

When a vector that does not include an expression regulatory sequence is used, an appropriate expression regulatory sequence is inserted upstream from the fusion protein gene.

The method of the present invention utilizes a phenomenon that, when a cell receives a stimulus such as stimulus by a drug, a transcription factor or cofactor in cytoplasm is specifically transported into a nucleus in response to the stimulus, and one of its objects is to clone a gene coding for such a transcription factor or cofactor. As means for achieving this object more efficiently, a cDNA library described below can be constructed.

A usual cDNA library includes many kinds of genes, and among them are genes coding for proteins that are transported into a nucleus without receiving any stimulus. As such proteins that are transported into a nucleus without receiving any stimulus, for example, structural proteins, which are components of the nucleus, can be mentioned. The structural proteins constituting a nucleus are synthesized in cytoplasm and then transported into the nucleus irrespective of presence or absence of a stimulus from the outside so as to function as components of the nucleus. There are many examples of the structural proteins constituting a nucleus, and these include proteins found in a structure called nuclear lamina considered to contain intermediate filaments supporting the inside of the nuclear membrane, histones and non-histone chromosomal proteins, which bind to DNA to play many roles, and so forth.

Accordingly, it becomes possible to efficiently obtain the object genes by constructing a library from which the aforementioned genes that may cause false positives in search of the object genes are eliminated beforehand. In the present invention, such a library from which genes that may cause false positives are eliminated is referred to as a cleaned library. It is preferred that unnecessary genes should be completely eliminated from the cleaned library, but even when the elimination is incomplete, the effect of the library can be sufficiently exhibited when most of such genes are eliminated.

An example of the method for constructing a cleaned library will be explained below. First, a library to be used as a base is constructed and introduced into cells to express fusion proteins therein. When GFP is used as a marker protein, localization of the fusion proteins can be detected by fluorescence of GFP. Further, the cells are fractioned by using a cell sorter without applying a stimulus such as stimulus by a drug. At this time, when genes coding for nucleus-constituting proteins or the like as described above are included, fusion proteins including such genes can be identified since these proteins are transported into nuclei even without a stimulus and the nuclei emit fluorescence. Since these cells of which nuclei emit fluorescence are not targeted, these are separated by using a cell sorter and removed. Since the remaining cell fraction does not include cells introduced with genes coding for proteins emitting fluorescence in a nucleus without a stimulus, these cells are collected, and plasmid DNAs are recovered from the fraction to construct a cleaned library. Thus, there are no or very few fusion proteins that are transported into the nucleus without a stimulus in the obtained cleaned library obtained as described above. Therefore, if the subsequent operations are performed by using this cleaned library, genes coding for proteins that are transported into nuclei in response to a stimulus such as stimulus by a drug can be efficiently obtained, and thus such a cleaned library is useful.

Further, many genes included in a cDNA library include those coding for proteins that are never transported into nuclei such as, for example, membrane proteins binding to cell membranes or proteins secreted out of the cells. Elimination of genes coding for such unnecessary proteins from the library beforehand is effective to improve efficiency in obtaining genes of proteins that are transported into nuclei in response to a stimulus such as stimulus by a drug, and such a library can also be included in the scope of the cleaned library.

An example of the method for constructing such a library will be explained below. There is a method for separating genes coding for proteins having a nuclear transport signal and genes coding for proteins not having the signal in an experiment system using yeast (Nature Biotechnology, 16, 1338–1342 (1998)). In this method, for example, genes having a nuclear transport signal such as a transcription factor NFκB and genes that do not have the signal can be separated. First, cDNA to be used as a base is prepared by reverse transcription of mRNA, cloned into vector described in the aforementioned reference and introduced into yeast to express proteins. Since this vector is designed so that auxotrophy should change and thus yeast can grow only when the expressed proteins are transported into nuclei, yeast colonies can be obtained only when the expressed proteins are transported into nuclei. When many of these colonies are collected and cloned cDNA are recovered from the colonies, there are no or very few proteins such as cell membrane proteins, which are not transported into the nuclei, among the encoded proteins. The cDNA thus obtained are cloned again into vectors GFP-F1, GFP-F2 and GFP-F3, which are described later, to construct a library. When a cleaned library constructed as described above is used to perform subsequent operations, genes coding for proteins that are transported into nuclei in response to a stimulus such as stimulus by a drug can be readily selected since genes that are not involved in the nuclear transport at all are eliminated. Thus, this cleaned library is useful.

As described above, there are various methods for constructing a cleaned library. Each of these may be solely employed, or a cleaned library may be first constructed by one method and then cleaning may be further performed repeatedly by other methods.

Further, since genome nucleotide sequences of various species including human have been elucidated, it has become possible to estimate genes coding for DNA binding proteins and transcription regulatory factors from genome nucleotide sequences by gene sequencing. For example, it has become possible to find genes coding for proteins having DNA-binding motifs such as zinc fingers among genome nucleotide sequences by bioinformatics. However, since computer analysis alone cannot show what functions these genes exhibit when expressed as proteins, it is necessary to express these proteins and perform experiments to analyze their functions. However, according to the present invention, the following experiment is enabled. First, a plurality of kinds of candidate genes that interest experimenters are listed based on bioinformatics or other information sources. The number of the candidate genes may be several dozens or several thousands, or even more. Then, based on information obtained from bioinformatics or the like, interesting genes can be collected by obtaining those provided by public institutions (for example, The Institute of Physical and Chemical Research (RIKEN), Tsukuba-shi) or commercially available cDNA. Then, a library of genes expressing GFP fusion proteins is constructed by using the collected candidate genes, and the present invention is carried out by using this library. Since the library is constructed by collecting candidate genes that interest the experimenters, nuclear transport proteins that interest the experimenters can be more efficiently detected. That is, since interesting genes are searched for in a small population that is limited beforehand, this method is efficient and useful as a method for carrying out the present invention.

Further, a nuclear membrane has a tunnel-like structure called a nuclear pore, which connects the inside of a nucleus and cytoplasm. Through the nuclear pore, substances are selectively transported into and out of the nucleus. Usually, a protein having a size of 40 kDa or larger cannot pass through the nuclear pore. However, when a protein has a special nuclear transport signal or is bound to a special protein that is responsible for transport, even a protein having a large size may be selectively transported into the nucleus. That is, it can be considered that passage through the nuclear pore is highly selectively regulated. On the other hand, small proteins may nonspecifically pass through the nuclear pore and flow into the nucleus.

In the examples of the present invention, GFP fusion proteins are used. GFP itself has a size of about 27 kDa. Therefore, if a protein fused with GFP is extremely small, the size of the whole fusion protein becomes not more than 40 kDa, and hence the fusion protein may flow into the nucleus nonspecifically. In this case, the nonspecific inflow increases false positives in gene search of the present invention.

Accordingly, in order to reduce false positives, the following procedure can be carried out. A nuclear export signal (Nature Biotechnology, 16, 1338–1342 (1998)) is incorporated into an amino acid sequence of a fusion protein to be expressed. Specifically, since the nuclear export signal is a short amino acid sequence, the incorporation can be carried out by adding a nucleotide sequence coding for the signal to a portion coding for the GFP fusion protein in the library. As a result, a GFP fusion protein having a nuclear export signal is expressed. Then, since this protein is actively discharged out of the nucleus by the nuclear export signal, a protein that nonspecifically flows into the nucleus due to diffusion can be eliminated out of the nucleus. As a result, false positives can be reduced.

When this method is used, true nuclear transport proteins are also pushed back out of the nucleus. However, since this is not the case where transport into the nucleus and transport out of the nucleus are balanced and no protein exists in the nucleus, fluorescence can be detected by a cell sorter and cells can be collected.

A gene library obtained as described above is introduced into appropriate eukaryotic cells. As the eukaryotic cells, animal cells, insect cells and plant cells can be mentioned. As the animal cells, there can be mentioned cell strains derived from tissues such as brain, muscles, placenta, pancreas and kidney of mammals such as human, monkey, mouse, rat and hamster. Specifically, there can be mentioned HepG2, which is an established cell line derived from human hepatoma (available from RIKEN Gene Bank Cell Bank, American Type Culture Collection (ATCC) or the like), COS-7, which is an established cell line derived from kidney of monkey (also available from RIKEN Gene Bank Cell Bank, American Type Culture Collection (ATCC) or the like) and so forth.

In order to introduce library DNA into aforementioned cells, methods usually used to introduce DNA into cultured cells such as the lipofection method, calcium phosphate method, DEAE dextran method, electroporation method, microinjection method, particle gun method and method using a virus vector can be used. Further, commercially available gene introducing reagents may also be used.

In the above-described operations, preparation of mRNA, preparation of cDNA by reverse transcription, ligation of a DNA fragment and a vector, introduction of a vector into a cell, expression of a gene and so forth can be performed according to general methods described in protocol collections such as Sambrook, J., Fritsch, E. F., and Maniatis, T., "Molecular Cloning A Laboratory Manual, Second Edition", Cold Spring Harbor Laboratory Press, 1.21 (1989). Further, libraries similar to the gene library of the present invention are described in Journal of Cell Biology, 146, 29–43 (1999) and so forth.

Subsequently, fusion proteins are expressed in transgenic cells to produce the fusion proteins. When a constitutional promoter is used as a promoter for expressing the fusion protein genes, no special operation is required. However, when a inducible promoter is used, an operation required for induction is performed.

(2) Step (b)

Subsequently, the transgenic cells are divided into two groups, and only cells of one group are stimulated so that nuclear transport proteins should be transported into nuclei.

The nuclear transport proteins are stimulated for the nuclear transport by a chemical substance, physiologically active substance, environmental change, contact with other cells or the like. As the chemical substance, there can be mentioned nutrients such as amino acids and fatty acids, dioxin, alcohol and so forth. As the physiologically active substance, tumor necrosis factor $\alpha$ (TNF$\alpha$), various interleukins, insulin, Fas Ligand and so forth. These substances include not only substances that have been reported for their stimulus for nuclear transport to date but also those expected to be discovered in future. Further, as the environmental change, there can be mentioned a thermal stimulus such as high or low temperature, pH change and so forth. As the "other cells", there can be mentioned contact of a killer cell with a target cell and so forth.

In this step, among the transgenic cells divided into two groups, a stimulus as described above is applied to cells of one group, but not to those of the other group. Application of a stimulus or no stimulus is a relative expression, and a case where a strong stimulus is applied to cells of one group and a weak stimulus is applied to cells of the other group is also encompassed in the scope of the present invention.

(3) Step (c)

In this step, for each of the stimulated cell group and the unstimulated cell group, localization of the fusion proteins in cells is detected based on the marker protein, and cells in which localization of the fusion proteins is observed in the nuclei or their nuclei are isolated.

The fusion proteins can be appropriately detected depending on the kind or property of the marker protein. For example, when a protein emitting self-fluorescence is used as the marker protein, the fusion proteins can be detected by observing fluorescence. When a protein catalyzing a color development reaction is used, cells can be immersed in a solution containing a substrate matching the protein, for example, when alkaline phosphatase is used, BCIP or NBT, which is a substrate for color development, and an enzymatic reaction can be allowed to obtain color development of a site in which the marker protein is localized. When an antigen peptide is used, cells can be immunostained by using a labeled antibody obtained by labeling an antibody binding to the antigen with a fluorescent dye such as FITC, TRITC or DTAF or an enzyme, and can be detected. Similarly, when a peptide such as avidin is used, it can also be detected in the same manner as in the method using an antigen by labeling a ligand such as biotin, which binds to avidin, with a fluorescent dye or an enzyme. These methods are usual cell biological methods, and there are many established methods. Further, the present invention is not limited to these methods, and any method may be used so long as the marker protein can be detected.

A specific detection method utilizing an antigen peptide as the marker protein will be exemplified below. Transgenic cells expressing the fusion proteins are immobilized with methanol, acetone, formaldehyde or the like. At this time, in order to clarify whether staining of the nuclei of the cells expressing the fusion proteins is present or absent, it is effective to allow the fusion proteins in the cytoplasm to flow out of the cells by treating the cells with digitonin prior to immobilization so that permeability of the cell membranes should be increased. After the cells are immobilized, they are rinsed with a buffer such as PBS, and then treated with an anti-peptide antibody diluted to an appropriate concentration. The anti-peptide antibody binds to an antigen peptide portion of the fusion protein. If this antibody is directly labeled with a fluorescent dye, localization of the fusion proteins can be detected by using the fluorescence as a marker, and whether the fusion proteins exist in the nuclei can be examined. Further, when the anti-peptide antibody is used as a primary antibody, and an antibody recognizing and binding to the primary antibody is used as a secondary antibody, luminosity is increased by an amplification effect and thus sensitivity can be improved.

Subsequently, cells in which localization of the fusion proteins in the nuclei is observed or their nuclei are isolated. Even when the fusion proteins are localized in the nuclei, the fusion proteins may exist in cytoplasm. In such a case, in order to clarify the presence or absence of fluorescence, color development or the like of the fusion proteins in the nuclei and thereby make identification reliable, it is preferred that the nuclei are isolated by disrupting the cells in order to separate the nuclei in which localization of the fusion proteins is observed. Further, it is also effective to allow the fusion proteins in the cytoplasm to flow out of the cells by treating the cells with digitonin or the like to increase permeability of the cell membranes.

The nuclei can be isolated by, for example, the method shown below (refer to "Methods of Cultured Cell Experiment for Molecular Biology Study", Yodosha, pp. 141–143). Cells are suspended in a buffer cooled with ice and disrupted on ice by using a homogenizer. The cell-disrupted suspension is overlaid on a buffer having an appropriate density and centrifuged so that only a nuclear fraction should be recovered as precipitates.

Cells in which fluorescence is detected in the nuclei or their nuclei can be isolated by cell sorting, flow cytometry, microdissection, microscopic observation or the like. Cell sorting is a method wherein a suspension of cells or their nuclei is made a thin flow so that the cells or their nuclei should flow in one line, and each cell or nucleus is successively irradiated with laser beams to detect fluorescence. When desired fluorescence is detected, an electric field is instantaneously applied to the cell or nucleus to blow the cell or nucleus horizontally so as to be collected in a tube. In the present invention, nuclei in which fluorescence is detected or cells containing such nuclei are collected. Cell sorting is an established technique, and a cell sorter, which is an apparatus used therefor, is commercially available.

Further, as another method, there can be mentioned a method of observing cells with a microscope, identifying desired cells and collecting the cells. An example of the method comprising collecting desired cells from many cells on a culture plate or slide glass will be explained below. Cells on a culture dish are collected by subjecting the cells that adhere to the dish to trypsin treatment and removing the cells. In order to minimize contamination of cells that are not the target cells at this time, trypsin can be injected into a plastic thin tube while a ring at an end of the tube is placed so that the target cells should be included, and the target cells and only a small number of cells around them can be removed from the dish and collected. Since cells are small, it is difficult to completely prevent contamination of surrounding cells that are not the target cells even when a thin tube is used, but isolation accuracy can be improved by repeating this isolating operation.

Further, excellent methods for collecting individual cells on a slide glass have already been developed. Similar systems are commercially available from a plurality of microscope manufacturers, but LM 200 Microdissection System available from Olympus Optical Co., Ltd. is most commonly used. This system is composed of an inverted microscope and an accompanying cell-collecting device. First, cells are observed with the microscope to identify the cells whose nuclei emit fluorescence. Then, the cells are irradiated with laser beams. A block of the cell-collecting device is brought into contact with cells from above, and the contact surface of the block with the cells is melted by heat of the laser and strongly adheres to cells. Since the light flux of the laser is narrowed to the size of cells, only the target cells can adhere to the block without contamination of surrounding cells. When a plurality of cells are to be collected, operations of observation, cell selection and laser irradiation are repeated. Then, when the block is finally lifted up, only cells desired to be collected adhere to the surface of the block and are lifted up together with the block. Thus, only the targeted cells can be collected.

Further, as another method, there is also a method of introducing a cell suspension into each well of a 96-well plate or 384-well plate so that a small number of cells should be added to each well, distinguishing cells showing desirable protein localization by microscopic observation, and collecting the cells from each well.

Further, any other methods can be used so long as localization of fusion proteins can be detected to isolate cells or their nuclei.

(4) Step (d)

In this step, genes coding for fusion proteins are recovered from isolated cells or their nuclei, and genes recovered from cells isolated from the stimulated cell group and genes recovered from cells isolated from the unstimulated cell group are compared. Genes can be recovered in the same manner as in usual recovery of plasmids from cells or their nuclei (refer to "Bio-Manual Series 3, Experimental Procedures for Gene Cloning", Yodosha, p.114–115). The genes can be compared by sequence analysis of a full-length or a part of a portion coding for a search object protein. Sequence analysis may be performed for the full length of a cloned fragment or only a partial region, for example, a fragment excised with a restriction enzyme.

As a result of comparison of the genes, a gene coding for a nuclear transport protein can be obtained by identifying a gene recovered only from the stimulated cell group or a gene recovered only from the unstimulated cell group.

A gene group obtained from the unstimulated cell group is considered to include genes coding for nucleoproteins constituting the nuclei and so forth. These proteins are fractioned as those transported into the nuclei since they are transported into the nuclei irrespective of presence or absence of a stimulus. On the other hand, the genes obtained from the stimulated cell group include genes coding for proteins that are transported into the nuclei in response to a stimulus, but also includes the aforementioned genes obtained from the unstimulated cell group. Thus, a gene coding for a protein which is transported into the nucleus specifically in response to a stimulus can be identified by comparing the genes obtained from these two cell groups.

Typically, sequence analysis is performed for all the obtained genes to list all the genes recovered from both the cell groups, and a gene found only in the stimulated cell group is identified. Since the gene found in this procedure is a gene coding for a protein which is transported into the nucleus only when a stimulus is applied, it is a gene coding for a transcription factor, cofactor or the like and considered to be an important gene. Thus, an important gene can be found.

As described above, a gene coding for a nuclear transport protein can be isolated or concentrated from the cDNA library. Further, in step (c), concentration of the object gene can be increased by repeating, for the isolated cells, the operations of detecting localization of fusion proteins in the cells utilizing the marker protein and isolating cells in which localization of the fusion proteins is observed in the nuclei or their nuclei.

<2> Utilization of the Present Invention

For example, there is an important cytokine protein called interferon γ, which stimulates a cell. This protein is present in blood, binds to a receptor on the outer surface of a cell membrane to transmit a signal into a cell and thereby induces various phenomena such as anti-viral activity of the cell. STAT1 protein is known as one of transcription factors for transmitting a signal of interferon γ from the receptor into the nucleus. It is known that, when a stimulus of interferon γ is applied, STAT1 in the cytoplasm is transported into the nucleus, binds to DNA and induces various gene expressions. As a result, anti-viral activity is obtained.

By utilizing the method of the present invention, transcription factors such as this STAT1 can be identified or obtained. Further, if an unknown transcription factor is transported into the nucleus in addition to STAT1 by the stimulus of interferon γ, it can also be found.

Thus, genes coding for proteins transmitting a signal into nuclei in response to various stimulus from the outside, which are important for life, can be identified by the present invention. These may include genes whose sequences have been known but whose functions are unknown, and novel transcription factors or cofactors that have been unknown to date can also be found.

Detection of the transcription factors or cofactors described above can be utilized for, for example, screening for development of drugs (anti-viral agents) for enhancing anti-viral activity. For example, if a novel transcription factor responsible for anti-viral activity is found by the present invention, a small molecule compound having an action for transporting the transcription factor into the nucleus can then be screened. Thus, there is given a possibility of developing drugs that enhance anti-viral activity by transporting the transcription factor into the nuclei.

Further, if, for example, a transcription factor involved in amelioration of diabetes mellitus is found, an antidiabetic drug can be developed by screening a drug that activates the transcription factor or transports it into the nuclei.

Further, if a transcription factor such as NFκB involved in Inflammatory reaction is found, a drug inhibiting Inflammation can be developed by screening a drug that blocks the nuclear transport so that the transcription factor should not be transported into the nuclei.

Further, if a transcription factor enhancing salt damage resistance or cold resistance of a plant is found, cold resistance or salt damage resistance can be enhanced by finding a method for transporting the transcription factor into the nuclei.

As described above, it is considered that, if a novel transcription factor or a novel function of a known transcription factor is found, it leads to screening of a novel drug or pharmaceutical agent, development of a genetically recombinant plant having improved characteristics by gene modification or the like, and so forth.

<3> Method for Screening Therapeutic Agent for Disease Caused by TNF Stimulus

The second aspect of the present invention is a method for screening a therapeutic agent for a disease caused by TNF stimulus and comprises the following steps of:

(a) preparing eukaryotic cells expressing a protein which is transported from cytoplasm into a nucleus through a nuclear pore in response to TNF stimulus;
(b) allowing TNF and a test substance to act on the eukaryotic cells;
(c) detecting a protein which is transported into the nucleus; and
(d) selecting a test substance that accelerates or inhibits the nuclear transport of the protein when the test substance is allowed to act on the cells in comparison to a case where the test substance is not allowed to act on the cells.

Hereafter, the aforementioned method will be explained step by step.

(1) Step (a)

First, eukaryotic cells expressing a protein which is transported from cytoplasm into nuclei through a nuclear pore in response to TNF stimulus are prepared. Such eukaryotic cells are, for example, cells introduced with a gene coding for a nuclear transport protein so that the protein should be expressed. These are typically cells harboring a gene identified as a gene coding for a nuclear transport protein by stimulating the nuclear transport protein so that it should be transported into a nucleus using TNF in the aforementioned method according to the first aspect of the present invention. If a fusion protein with a marker protein whose localization in a cell can be detected is used as the nuclear transport protein, the nuclear transport of the nuclear transport protein can be detected by using the marker. As the marker protein and the method for detecting the marker, the same ones as in the first aspect of the invention can be used. Further, specific examples of the nuclear transport protein include the proteins shown in Table 9 described later, but they are not limited to them. Gene products that can be selected by the first aspect of the invention can be preferably used.

(2) Step (b)

Subsequently, TNF and a test substance are allowed to act on the eukaryotic cells. In order to allow the test substance to act on the eukaryotic cells, for example, cells can be immersed in a solution of a test substance so that the substance should be taken into the cells from the outside of the cells, or the eukaryotic cells can be transformed with a foreign gene that is not a gene coding for the nuclear transport protein so that the gene should be expressed. In the latter method, the expression product of the foreign gene serves as the test substance. As such eukaryotic cells, transformants transformed with a gene library can be mentioned.

In this step, eukaryotic cells on which the test substance is not allowed to act, but only TNF is allowed to act are prepared as a control. If the gene library is constructed by using a vector including a-promoter capable of regulating expression, presence or absence of the test substance can be controlled. The library can be constructed in the same manner as in the first aspect of the invention.

(3) Step (c)

In the eukaryotic cells on which TNF is allowed to act in the step (b), localization of the nuclear transport protein in the cells is detected. This operation can be performed in the same manner as in the detection of localization of the fusion proteins in the cells in the first aspect of the invention.

(4) Step (d)

Subsequently, there is selected a test substance that accelerates or inhibits the nuclear transport of the nuclear transport protein when the test substance is allowed to act on the cells in comparison to the case where the test substance is not allowed to act the cells.

The substance selected in this step is a substance that specifically inhibits or accelerates the nuclear transport of the nuclear transport protein or a substance that inhibits or accelerates production of the nuclear transport protein itself.

Further, a substance that accelerates or inhibits the nuclear transport of the nuclear transport protein can be obtained based on the gene sequence of the nuclear transport protein. If a known nuclear transport signal sequence is found in the gene sequence, a substance binding to the sequence is designed. Further, if a known nuclear transport signal sequence is not found in the gene sequence, the gene sequence is partially deleted to identify a site for inhibiting nuclear transport, and a substance binding to this site is designed. As such a substance, for example, anti-sense DNA or ribozyme can be mentioned. Further, a signal specific for TNF can also be enhanced by introducing a gene coding for a nuclear transport protein into the cells. Furthermore, a protein that binds to a nuclear transport protein can be obtained by the yeast two-hybrid method or the like, and a substance inhibiting binding of the two can be screened or designed.

By administering a substance obtained by the method of the present invention together with TNF to a liver cell strain, primary culture liver cell or animal, for what diseases the substance should be developed as a therapeutic agent can be known depending on what actions of TNF are inhibited or accelerated. As the TNF actions, release of cytokine, cell growth, cell differentiation, apoptosis induction, gene expression induction and so forth can be mentioned depending on the target cells. Release of cytokine can be detected by measuring the cytokine by the ELISA method. Further, cell growth can be determined based on, for example, uptake of isotope-labeled thymidine. Cell differentiation can be determined by, for example, staining a differentiation marker with an antibody and measuring it by FACS. Apoptosis induction can be determined by, for example, the tunnel method. Induction of gene expression can be determined by, for example, using a gene chip or PCR.

Specific examples of the targeted diseases of the method of the present invention include liver diseases such as acute hepatitis, chronic hepatitis, fulminant hepatitis, liver fibrosis, cirrhosis and liver cancer, and there can be further mentioned Crohn's disease, multiple secrosis, chronic rheumatoid arthritis, systemic vasculitis, septic shock, diabetes mellitus (insulin resistant) and so forth.

By combining the first and second aspects of the invention, a gene coding for a nuclear transport protein can be retrieved, and a therapeutic agent for a disease caused by TNF stimulus can be screened by using the identified gene.

BEST MODE FOR CARRYING OUT THE INVENTION

Figure 1:
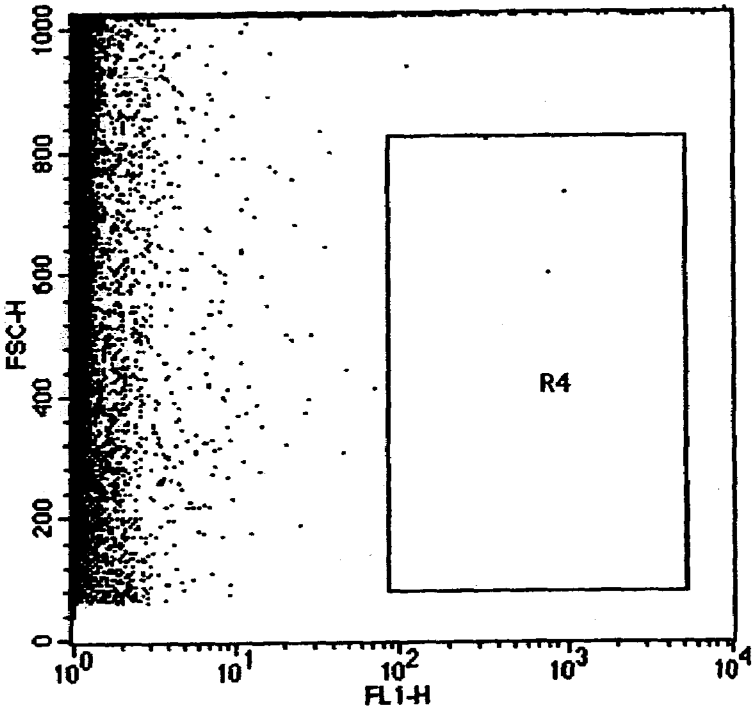
FIG. 1 shows distribution of nuclei of HepG2 cells determined by cell sorting. The vertical axis represents FSC (size), and the horizontal axis represents FL1 (fluorescence intensity).

Hereafter, the present invention will be explained more specifically with reference to examples.

EXAMPLE 1

Validation of Cloning Model System of Genes for Nuclear Transport Proteins by Utilizing Nuclear Transport Signal Sequence of SP-H Antigen Known for Nuclear Transport in Unstimulated Cells <1> Construction of GFP Expression Vector and Vector Expressing Fusion Protein of GFP and Nuclear Transport Signal As the frame structure of the vectors, a commercially available plasmid vector pQBI-25 (6238 bp, Takara Shuzo, Catalog Code 3131, its nucleotide sequence is described in was partially modified and used.

The modification was performed as follows.

(1) Into the nucleotide sequence of pQBI-25 shown as SEQ ID NO: 1, 4, nucleotides, GATC, were inserted between nucleotide numbers 16 and 17. By this operation, the restriction enzyme BglII site of the nucleotide numbers 12 to 17 was disrupted. Specifically, this operation was performed as follows.

In an amount of 20 ng of pQBI-25 was digested with a restriction enzyme BglII and treated with T4 DNA polymerase in the presence of DNTP (mixture of dATP, dGTP, dCTP and dTTP) to blunt-end the BglII-digested ends. Subsequently, self-cyclization was allowed by using a DNA ligase (Takara Shuzo, DNA Ligation Kit Ver.1 No. 6021). The obtained vector DNA was amplified in *Escherichia Coli* (*E. coli*), then purified, digested with restriction enzymes SacII and XbaI and used for a ligation reaction described later.

(2) C of the nucleotide number 1125 positioned around in the middle of the GFP gene was replaced with T. By this operation, while the encoded amino acid (Cys) remained unchanged, the recognition site of the restriction enzyme BsgI (nucleotide numbers 1122–1127) was disrupted. Specifically, the following operation was performed.

In order to convert the sequence of the BsgI site in the GFP gene, ctgcac, into ctgtac, a primer for PCR (GFP-broken BsgI) having the following sequence was prepared. The sequence of its corresponding primer, pCMV4-855S, is also shown below.

```
[Sequences of GFP-broken BsgI]   (SEQ ID NO: 2)
TGTTGGCCATGGAACAGGCAGTTTGCCAGTAGTACAGAT

[pCMV4-855S]                     (SEQ ID NO: 3)
GGTAGGCGTGTACGGTG
```

PCR was performed by using these two primers and 10 ng of pQBI-25 DNA as template DNA. An amplicon (amplification product) had the sequence of the primer GFP-broken BsgI at one end, and thereby the original BsgI site was converted into ctgtac. However, the encoded amino acid sequence was unchanged, and, after protein expression, a peptide having the same amino acid sequence could be obtained. Subsequently, the obtained amplicon was treated with restriction enzymes NcoI and SacII to obtain a fragment of about 180 bp.

(3) In order to disrupt a stop codon in the GFP gene and provide a cDNA cloning site at that position, nucleotide numbers 1696–1780 were replaced with each of the following DNA fragments. These inserted fragments have different length by one base each, and thereby they can correspond to 3 kinds of reading frames of the nucleotide sequence.

```
                        (SEQ ID NO: 4)
  GTGCAGATCTGATTGAATGATATCGGATCCTCTAGA

                        (SEQ ID NO: 5)
 AGTGCAGATCTGATTGAATGATATCGGATCCTCTAGA

                        (SEQ ID NO: 6)
AAGTGCAGATCTGATTGAATGATATCGGATCCTCTAGA
```

Specifically, the following procedure was performed.

Three kinds of primers having the following sequences were synthesized.

```
[GFP(-)F1]  GCTCTAGAGGATCCGATATCATTCAATCAGATCTGCACGTTGTACAGTTCATCCA   (SEQ ID NO: 7)

[GFP(-)F2]  GCTCTAGAGGATCCGATATCATTCAATCAGATCTGCACTGTTGTACAGTTCATCCA  (SEQ ID NO: 8)

[GFP(-)F3]  GCTCTAGAGGATCCGATATCATTCAATCAGATCTGCACTTGTTGTACAGTTCATCCA (SEQ ID NO: 9)
```

These primers were incorporated with the restriction enzyme BsgI and BglII sites, each of 3 stop codons whose reading frames were shifted and restriction enzyme EcoRV, BamHI and XbaI sites in this order from the 3' end. PCR was performed by using each of these primers and the aforementioned primer pCMV4-855S in the same manner as described above to obtain 3 kinds of amplicons. These amplicons were treated with the restriction enzymes NcoI and XbaI to obtain 3 kinds of fragments of about 620 bp.

The SacII-XbaI fragment obtained in the above (1), the fragment of about 180 bp obtained in the above (2) and 1 kind out of the 3 kinds of fragments of 620 bp obtained in the above (3) were mixed to allow a ligation reaction. DNA after the reaction was transfected into competent cells of *E. coli* JM109. Plasmid DNAs were recovered from the transformants and sequence analysis was performed to select those having the target sequences, that is, those in which the BsgI site and the stop codon unique to the GFP gene were disrupted and which had a cloning site downstream from the gene were selected. The three kinds of plasmids thus obtained were designated as GFP-F1, GFP-F2 and GFP-F3. In GFP-F1, GFP-F2 and GFP-F3, the sequence of the nucleotide numbers 1696–1780 of pQBI-25 is replaced with the sequence of SEQ ID NO: 4, 5 or 6, respectively. The nucleotide sequence of GFP-F3 is shown as SEQ ID NO: 10. GFP-F1 corresponded to GFP-F3 lacking the nucleotides of the nucleotide numbers 1700 and 1701, and GFP-F2 corresponded to GFP-F3 lacking the nucleotide of the nucleotide number 1700.

Subsequently, a gene fragment coding for the SP-H antigen having a nuclear transport signal was cloned into the GFP-F2 expression vector. The gene fragment coding for the SP-H antigen was obtained by performing PCR using cDNA obtained by reverse transcription of mRNA purified from the HepG2 cell as a template and the following primers. The nucleotide sequence of the SP-H antigen gene is registered in GenBank with an accession number Z11583.

```
[SP-H-3234]
cagagcagatcttgagatgcggctgcagaacg   (SEQ ID NO: 11)

[SP-H-6548]
cagcatctagaacacaggtggggccactcactgg (SEQ ID NO: 12)
```

An amplicon of about 3300 bp was obtained by the aforementioned PCR. This amplicon included a portion cording for the nuclear transport signal of the SP-H antigen (refer to "Primary structure and microtubule-interacting domain of the SP-H antigen: a mitotic map located at the spindle pole and characterized as a homologous protein to NuMA", T. Maekawa and R. Kuriyama, Journal of Cell Science 105: pp. 589–600, 1993).

Subsequently, the above amplicon was treated with the restriction enzymes BglII and XbaI, and the obtained gene fragment was cloned into the expression vector GFP-F2 similarly treated with the restriction enzymes BglII and XbaI. The expression vector including the gene coding for the fusion protein of GFP and the SP-H antigen thus constructed was designated as GFP-F2-SP-H. If GFP-F2-SP-H is transfected into a cell, the fusion protein of GFP and the SP-H antigen is expressed in the cell, and the expressed fusion protein moves into the nucleus due to the nuclear transport signal of the SP-H antigen. Further, the expression vector GFP-F2, which does not include the SP-H antigen, expresses the GFP protein, but since the protein does not have the nuclear transport signal, the expressed GFP protein is dispersed in the cytoplasm.

<2> Introduction of GFP Expression Vector into Human Established Cell Line

The GFP expression vector and the vector expressing the fusion protein of GFP and the SP-H antigen prepared as described above were introduced into a human established liver cell HepG2.

$1.5\times10^6$ of HepG2 cells (obtained from American Type Culture Collection, ATCC HB8065) were inoculated on a plate having a diameter of 100 mm and cultured overnight in a MEM medium containing 10% FBS at 37° C. in 5% $CO_2$ under a moist condition. By using FuGene™ 6 (Roche, Product No. 1 814 443) as a vector-introducing reagent, the HepG2 cells were introduced with each vector. In an amount of 22.5 μl of FuGene was gradually suspended in 727.5 μl of a serum-free MEM medium and left stand at room temperature for 5 minutes. Then, 750 μl of this FuGene-MEM suspension was added with 7.5 μg of each vector DNA, slowly mixed, and left stand at room temperature for 15 minutes. This suspension was added to the HepG2 cells and the cells were cultured overnight at 37° C. in 5% $CO_2$ under a moist condition. In order to confirm the introduction of each vector, the cells were removed with 2.5% trypsin-EDTA, washed with PBS and then resuspended in PBS. The number of cells and color development of GFP were counted under a fluorescence microscope by using a blood cell counting chamber. As a result, GFP color development was observed in about 10% of cells.

<3>Isolation of Nuclei

The nuclei were isolated from the HepG2 cells introduced with the GFP expression vector and the vector expressing the fusion protein of GFP and the SP-H antigen according to a known method (refer to "Method of Cultured Cell Experiment for Molecular Biology Study", Yodosha, pp. 141–143). The cells prepared in the above <2> were suspended in ice-cooled Buffer A (Table 1) at $5\times10^6$ cells/ml, left stand on ice for 10 minutes, then transferred to an ice-cooled Dounce homogenizer and disrupted at 30 strokes. The resultant was centrifuged at 2,500×g at 4° C. for 5 minutes, the supernatant was discarded, and the precipitates were suspended in ice-cooled Buffer B (Table 2) at $1\times10^7$ cells/ml. The cells were disrupted again at 30 strokes by the ice-cooled Dounce homogenizer. The same amount of ice-cooled Buffer C (Table 3) was added to a centrifuging tube, and the homogenate was overlaid on the layer. This was centrifuged at 3,000×g at 4° C. for 10 minutes, and the supernatant was removed to obtain precipitated nucleus fractions.

TABLE 1

| Composition of Buffer A | |
|---|---|
| 10 mM | HEPES-KOH (pH 7.9) |
| 1.5 mM | $MgCl_2$ |
| 10 mM | KCl |
| 1 mM | DTT |
| 0.5 mM | PMSF (added as required) |

TABLE 2

| Composition of Buffer B | |
|---|---|
| 0.25 M | Sucrose |
| 10 mM | Tris-HCl (pH 7.9) |
| 5 mM | $MgCl_2$ |
| 1 mM | DTT |
| 0.5 mM | PMSF (added as required) |
| 0.1% | Triton X-100 |

TABLE 3

| Composition of Buffer C | |
|---|---|
| 0.5 M | Sucrose |
| 10 mM | Tris-HCl (pH 7.9) |
| 5 mM | $MgCl_2$ |
| 1 mM | DTT |
| 0.5 mM | PMSF (added as required) |
| 0.1% | Triton X-100 |

<4> Sorting by Using Flow Cytometer

Figure 2:
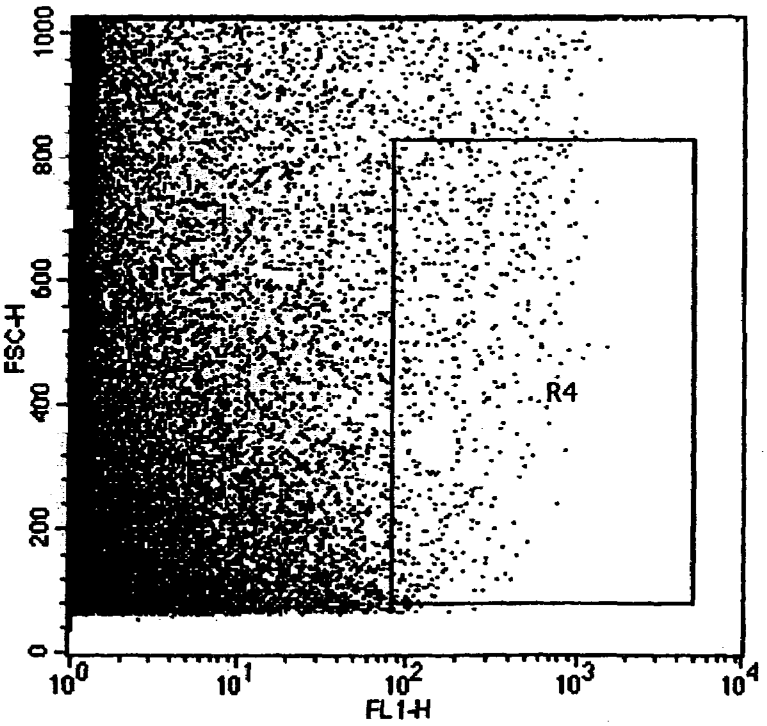
FIG. 2 shows distribution of nuclei of HepG2 cells introduced with a vector expressing a fusion protein of GFP and the SP-H antigen.
Figure 3:
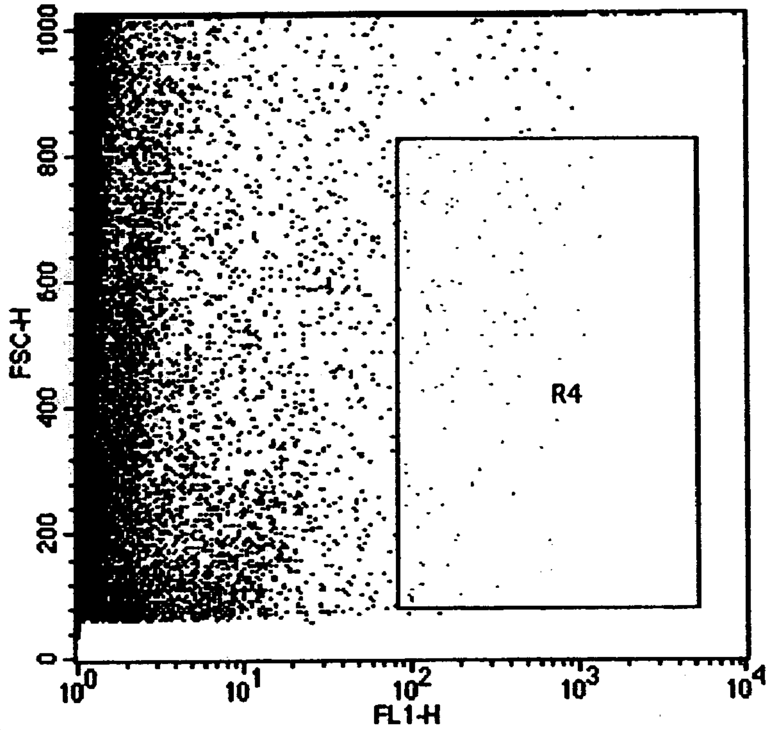
FIG. 3 shows distribution of nuclei of a sample for sorting (a mixture in which the ratio of nuclei of cells introduced with a GFP expression vector and a vector expressing a fusion protein of GFP and the SP-H antigen is 49:1).

Each nucleus fraction obtained in the above <3> was suspended in FACSFlow (Becton Dickinson, Product No. 342003) at $0.5\times10^6$ nuclei/ml. Nuclei of cells introduced with the GFP expression vector and the vector expressing the fusion protein of GFP and the SP-H antigen were mixed at a ratio of 49:1 and used as a sample for sorting. Sorting was performed by using a cell sorter FACSVantageSE (Becton Dickinson). The results are shown in FIGS. 1 and 2. FIG. 1 shows distrubution of nuclei for the control (nuclei of the HepG2 cells). FIG. 2 shows distribution of nuclei of the HepG2 cells introduced with the vector expressing the fusion protein of GFP and the SP-H antigen. The vertical axis represents FSC (size), and the horizontal axis represents FL1 (fluorescence intensity). From the results shown in FIGS. 1 and 2, R4 was used as the sort gate (see FIGS. 1 and 2), and the sorting conditions were established as shown in Table 4. Under these conditions, $2.1\times10^6$ of samples for sorting were subjected to the sorting. As a result, 124 nuclei within the range defined by the sort gate were isolated (FIG. 3).

TABLE 4

| Sorting conditions | |
|---|---|
| Droplet delay | 13–15 |
| Deflected drops | 3 |
| Sort mode | Enrich |
| Sample flow rate | 1200 counts/sec |

<5>Preparation of Plasmids from Nuclei

In order to verify vectors included in the nucleus fractions obtained by sorting in the above <4>, plasmids were prepared from the nuclei.

In an amount of 400 μl of a Hirt solution (0.6% SDS, 10 mM EDTA) was added to a tube containing each of the sorted nucleus fractions, the inner wall of the tube was washed well, and the solution was left at room temperature for several minutes. Subsequently, the solution was added with 100 μl of 5 M NaCl and cooled overnight on ice. The solution was centrifuged at 15000 rpm at 4° C. for 20 minutes, and its supernatant was centrifuged again at 15000 rpm at 4° C. for 10 minutes. The plasmids in the obtained supernatant were extracted with a phenol/chloroform solution and further extracted with chloroform. Since it was expected that plasmids would be obtained in a trace amount, glycogen was added to perform ethanol precipitation.

<6>Verification of Plasmid

In order to verify the ratio of the GFP expression vector and the vector expressing the fusion protein of GFP and the SP-H antigen constituting the plasmids obtained in the above <5>, *E. coli* was transformed with the obtained plasmids, and colony PCR was performed for the obtained colonies of transformants to identify the kinds of the vectors.

(1) Transformation of *E. coli* with Collected Plasmids

The plasmids obtained in the <5> were suspended in 10 μl of distilled water. In an amount of 2 μl of the plasmid solution and 20 μl of competent cells (*E. coli* competent cells, ELECTRO MAX™ DH12S™ (GIBCO BRL, Product No. 18312–017)) were mixed and transferred into a micro chamber for electroporation, and electroporation was performed under conditions of a voltage of 1.8 kV, capacitance of 25 μF and impedance of 200 U.

Cells were immediately collected from the chamber, suspended in 0.5 ml of SOC medium (Table 5) and shaken at 37° C. for 1 hour at 210 rpm. In an amount of 100 μl of the mixture was applied to an LB plate containing 100 μg/ml ampicillin and incubated overnight at 37° C. As a result, colonies were obtained at 30 cfu per 1 μl of the plasmid solution.

TABLE 5

| Composition of SOC medium | |
|---|---|
| Bacto trypton (Difco) | 20 g/L |
| Yeast extract (Difco) | 5 g/L |
| NaCl | 10 mM |
| KCl | 2.5 mM |
| $MgSO_4$ | 10 mM |
| $MgCl_2$ | 10 mM |
| Glucose | 20 mM |

(2) Colony PCR and Agarose Gel Electrophoresis

In order to verify the plasmids obtained in the above <6>, colony PCR and agarose gel electrophoresis were performed for 40 colonies. As the primers, the following sequences were used.

```
[pQBI-1621S]
aagagagaccacatggtcct         (SEQ ID NO: 13)

[pQBI-1977AS]
ccagaatagaatgacacctactc      (SEQ ID NO: 14)

[SP-H-3632AS]
gccttccactcatcttcagcctt      (SEQ ID NO: 15)
```

The colony PCR was performed by using Taq DNA Polymerase (Amersham Pharmacia Biotech, Product No. T0303Z) in a reaction mixture having a composition shown in Table 6. The reaction conditions were as follows: 94° C. for 1 minute 94° C. for 20 seconds, 55° C. for 1 minute, 72° C. for 1 minute, for 40 cycles 72° C. for 5 minutes 4° C.

TABLE 6

| Composition of PCR reaction mixture (per tube) | |
|---|---|
| Template | 1 colony |
| Taq DNA polymerase | 0.05 μl |
| DNTP (2.5 mM each) | 0.8 μl |
| 10 × buffer (attached to above enzyme) | 1 μl |
| 10 μM PCR primer solution | 3 μl |
| Purified water | 5.15 μl |

In an amount of 3 μl of each sample obtained by the colony PCR were subjected to agarose electrophoresis. As a result, 36 colonies out of 40 colonies harbored the vector expressing the fusion protein of GFP and the SP-H antigen, and 3 colonies harbored the GFP expression vector. This result indicated that the vector expressing the fusion protein of GFP and the SP-H antigen was concentrated 45 times.

From the above result, it was found that a small amount of the target fraction contained in the sample could be efficiently concentrated. That is, this result indicates that nuclei emitting GFP fluorescence could be efficiently concentrated from a large number of nuclei. Further, it is also indicated that plasmid DNA could be collected from the obtained nucleus fraction, and that, after transfection into *E. coli*, colonies could be obtained. Plasmid DNA can be obtained from these colonies in an amount sufficient for subsequent experiments.

The above results revealed that, when the GFP fusion protein moved into nuclei in response to a stimulus such as stimulus by a drug, the nuclei could be isolated by the aforementioned method to collect plasmid DNA included in the nuclei, and that the method of the present invention was feasible.

EXAMPLE 2

Search of Protein which is Transported into Nucleus only with Stimulus

Proteins which is transported into nuclei with a stimulus were searched for by inserting a human cDNA library into the GFP expression vector to construct vectors expressing fusion proteins of proteins encoded by the cDNA and GFP.

<1> Construction of Vector Expressing GFP and cDNA Library

A human normal liver cDNA library (Premade cDNA Library, Invitrogen, Product No. A550–42) was cloned into the three kinds of GFP expression vectors GFP-F1, GFP-F2 and GFP-F3 prepared in Example 1.

A glycerol stock of *E. coli* introduced with the pcDNA3.1-Uni vector inserted with the cDNA library was inoculated on an LB plate containing 100 μg/ml of ampicillin and cultured at 37° C. for 16 hours to obtain colonies. The obtained $1.7\times10^7$ colonies were collected, and the plasmids were purified by using QIAGEN-tip500 (QIAGEN, Product No. 12162). The inserted cDNA fragments were amplified from the obtained plasmids by PCR using primers having the following sequences. The reaction was performed by using a reaction mixture having the composition shown in Table 7 under the following conditions: 94° C. for 1 minute 94° C. for 20 seconds, 55° C. for 30 seconds, 68° C. for 5 minutes, for 40 cycles 68° C. for 10 minutes 4° C.

[pcDNA-911S]
aagcttggtaccgagctcggatccactattccagtgtg (SEQ ID NO: 16)
[pcDNA-1015AS]
aactagaaggcacagtcgaggctgatca (SEQ ID NO: 17)

TABLE 7

| Composition of PCR reaction mixture (per tube) | |
|---|---|
| Template (plasmid) | 10 ng |
| LA Taq | 0.05 μl |
| dNTP (2.5 mM each) | 0.8 μl |
| 5 × buffer (attached to above enzyme) | 10 μl |
| 10 μM PCR primer solution | 2 μl |
| Perfect Match* | 1 μl |
| Purified water | 28.45 μl |

*Manufactured by Stratagene, Product No. 600129-81

Each of the obtained amplicon was digested with restriction enzymes BamHI and XbaI. Subsequently, the obtained gene fragment was cloned into the expression vectors GFP-F1, GFP-F2 and GFP-F3 digested with the restriction enzymes BglII and XbaI. Thus, an expression vector including a gene expressing a fusion protein of GFP and a protein encoded by the human normal liver cDNA library was constructed.

Subsequently, each vector thus constructed was transfected into *E. coli* competent cells (ELECTRO MAX™ DH12S™ (GIBCO BRL, Product No. 18312-017)) and cultured overnight, and then plasmid DNA was purified to obtain plasmid DNA in an amount sufficient to perform the following operations.

<2> Introduction of Expression Vector into Human Established Cell Line

The vectors expressing fusion proteins of GFP and the cDNA library prepared as described above was introduced into the human established liver cell line HepG2 as in the same manner as in Example 1.

<3> TNFα Stimulus

Two days after the introduction of vectors in the above <2>, the transformed cells were added with TNFα. The medium was removed from the culture broth of the transformed cells and the cells were washed with PBS, added with a medium consisting of MEM medium containing 0.5% FBS added with 100 ng/ml TNFα and cultured under a moist condition at 37° C. in 5% $CO_2$ for 4 hours. As a control, the transformed cells were similarly cultured in a MEM medium containing 0.5% FBS not containing TNFα.

<4>Isolation of Nuclei

Nuclei were isolated from the transformed cells of the TNFα-stimulated group and the control group prepared as above in the same manner as in Example 1.

<5>Sorting by Using Flow Cytometer

Figure 4:
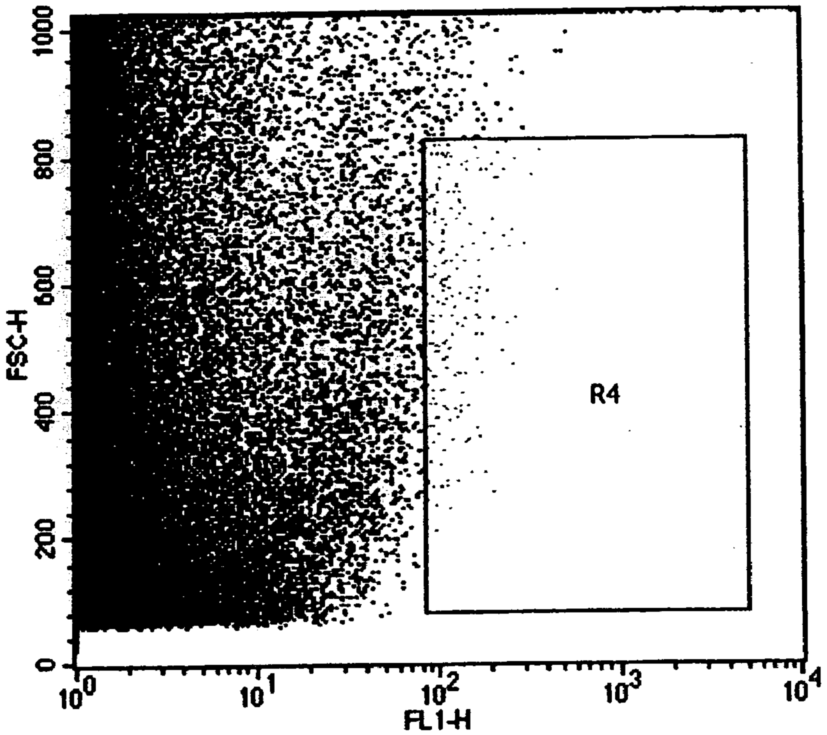
FIG. 4 shows distribution of nuclei of transformed cells of the TNFα-stimulated group.
Figure 5:
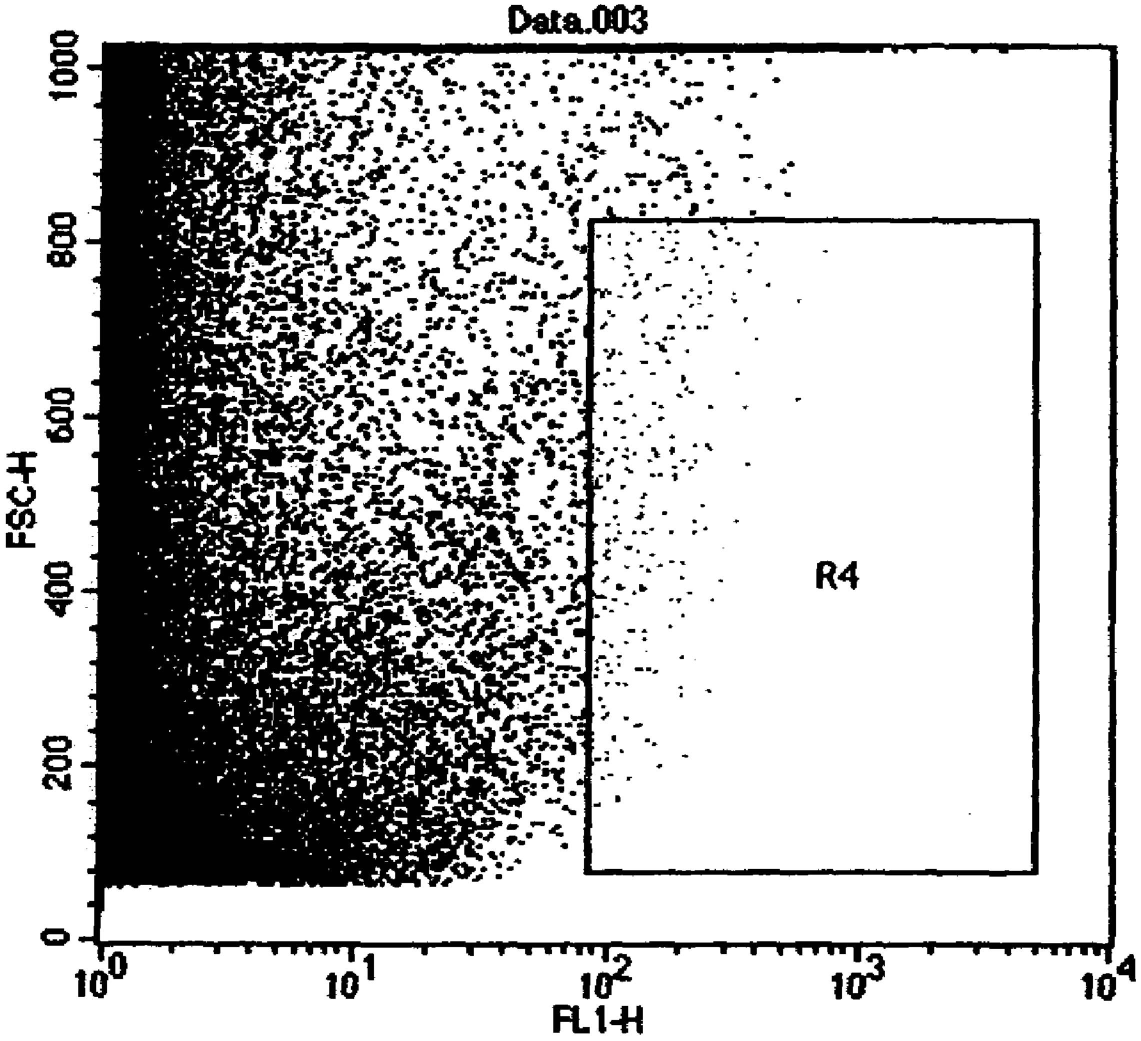
FIG. 5 shows distribution of nuclei of transformed cells of a control group.

Each of the obtained nucleus fraction was suspended in FACSFlow (Becton Dickenson, Product No. 342003) at $0.5\times10^6$ nuclei/ml and subjected to sorting. Sorting was performed under the same conditions as in Example 1. Sorting was performed for $4.0\times10^6$ nuclei in each of the TNFα-stimulated group (FIG. 4 ) and the control group (FIG. 5).

As a result, 228 nuclei (FIG. 4) and 332 nuclei (FIG. 5) within the range defined by the sort gate were obtained.

<6> Preparation of Plasmids from Nuclei

In order to verify the vectors included in the nucleus fractions obtained by sorting, plasmids were prepared from the nuclei in the same manner as in Example 1.

<7> Verification of Plasmids

In order to verify cDNA inserts inserted in the plasmids obtained as above, *E. coli* was transformed with the collected plasmids, and colony PCR was performed for the obtained colonies to determine the nucleotide sequences of the inserts.

(1) Transformation of *Escherichia Coli* with Collected Plasmids

Transformation was performed in the same manner as in Example 1. As a result, colonies were obtained at 63 cfu per 1 μl of the plasmid solution from the TNFα-stimulated group, and at 117 cfu per 1 μl of the plasmid solution from the control group.

(2) Colony PCR and Agarose Gel Electrophoresis

In order to analyze the inserts for the colonies obtained as above, 240 colonies of the TNFα-stimulated group and 336 colonies of the control group were subjected to colony PCR and agarose gel electrophoresis. As the primers, the following sequences were used.

[pQBI-1621S] supra (SEQ ID NO: 13)

[pQBI-1841AS] aggcacagtcgaggctg (SEQ ID NO: 18)

Colony PCR was performed by using LA Taq (Takara Shuzo, Product No. RR002B) and a reaction mixture having the composition shown in Table 8. The reaction conditions were as follows: 94° C. for 1 minute 94° C. for 20 seconds, 53° C. for 30 seconds, 72° C. for 5 minutes, for 40 cycles 72° C. for 10 minutes 4° C.

TABLE 8

| Composition of PCR reaction mixture (per tube) | |
|---|---|
| Template | 1 colony |
| LA Taq | 0.05 μl |
| dNTP (2.5 mM each) | 1.6 μl |
| 5 × buffer (attached to above enzyme) | 2 μl |
| 10 μM PCR primer solution | 0.4 μl |
| Purified water | 6 μl |

In an amount of 3 μl of each sample obtained by colony PCR was subjected to agarose electrophoresis to confirm that PCR amplification was attained.

<7> Determination of Nucleotide Sequence of Insert

In an amount of 0.8 μl of a solution obtained by diluting 4-fold the above PCR reaction mixture with purified water was added with 0.12 μl each of Exonuclease I and shrimp-derived alkaline phosphatase (commercially avalable from USB as PCR Product Presequencing kit, Product No. US70995), further added with 2.76 μl of 1×LA Taq buffer (Takara Shuzo, attached to Product No. RR002B), allowed to react at 37° C. for 30 minutes and heated at 80° C. for 15 minutes. In an amount of 3.8 μl of the reaction mixture was added with 0.8 μl of 1.6 μM pQBI-1621S (supra, SEQ ID NO: 13) as a primer for a sequencing reaction and 3 μl of a mixture for a sequencing reaction (PE Applied Biosystem, trade name: Big Dye), and a sequencing reaction was performed under the following conditionzs: 96° C. for 2 minutes 96° C. for 10 seconds, 50° C. for 5 seconds, 60° C. for 4 minutes, for 30 cycles 4° C.

After completion of the reaction, unreacted components were removed from the reaction mixture by gel filtration using Sephadex-G50, and the collected fraction was heated and dried. The obtained DNA was added with 7.5 μl of purified water and dissolved, and this DNA solution was heated at 90° C. for 2 minutes and subjected to sequencing by a capillary sequencer ABI 3700 (PE Applied Biosystems).

The obtained nucleotide sequences were searched for by collation with an external database UniGene. As a result, 67 kinds of proteins from the TNFα-stimulated group (including 19 kinds of proteins whose function was unknown) and 120 kinds of proteins from the control group were obtained.

Further, proteins found only in the TNFα-stimulated group included a novel zinc finger protein, which was expected to be a kind of a transcription factor based on the motif analysis of the amino acid sequence. Further, a gene coding for an unknown protein, which was estimated to be a transcription initiation factor inhibiting gene expression was also found in the TNFα-stimulated group. Furthermore, the proteins similarly found only in the TNFα-stimulated group included 11 kinds of EST and 6 kinds of proteins whose function was unknown, and thus unknown genes were successfully isolated.

<8> Verification of Nuclear Transport of Proteins Retrieved by Method of the Present Invention in Response to TNFα Stimulus As described above, the genes coding for proteins that are transported into the nuclei by TNFα stimulus were obtained. Then, examinations were further performed, and about 40 kinds of genes were obtained in total. Then, 12 kinds of proteins arbitrarily selected from them were verified by another method to see whether they were surely transported into the nuclei. The 12 kinds of protein gene are shown in Table 9. Further, UniGene numers for those of human are shown below.

| | | | |
|---|---|---|---|
| 1) Hs.12303, | 2) Hs.183180, | 3) Hs.198246, | 4) Hs.83849, |
| 5) Hs.76722, | 6) Hs.74034, | 7) Hs.129959, | 8) Hs.24301, |
| 9) Hs.24756, | 10) Hs.161137, | 11) Hs.348609, | 12) Hs.24608 |

Fusion genes obtained by ligating each of these genes with the GFP gene were transfected into the HepG2 cells by the method described in Example 1 and above. These 12 kinds of genes were expressed as fusion proteins with GFP in cells after transfection. Whether each fusion protein was actually transportred into the nuclei was verified by a method other than the aforementioned method.

TABLE 9

| | | | |
|---|---|---|---|
| 1 | Hs.12303 | Homologue of Ty (*S. cerevisiae*) 6 suppressor | Chromatin structure regulating factor, regulating transcription |
| 2 | Hs.183180 | Ana-phase acceleration factor complex subunit 11 | |
| 3 | Hs.198246 | Vitamin D-binding protein | TNF-α reduces binding of RXR/vitamin D receptor to vitamin D responding factor. |
| 4 | Hs.83849 | Human homologue of drosophila Flightless-I gene product | N-terminus leucine-rich domain having 52% homology with human gelsolin protein (16 continuous leucine-rich repeats) LRR protein family, for example, mammal rsp1 (Ras-mediated signaling), yeast adenylate cyclase TRIP: Nucleic Acids Res 1998 Aug 1; 26(15): 3460–7, LRRFIP1 and 2: Genomics 1999 Jun 1; 58(2): 146–57 |
| 5 | Hs.76722 (BF197559) | CCAAT/enhancer binding protein, Delta | |
| 6 | Hs.74034 (Hs.76320) | Caveolin 1 | |
| 7 | Hs.129959 | Virtual protein MGC 10763 | |
| 8 | Hs.24301 | Polymerase (RNA) II polypeptide E | Existing in nucleoplasm |
| 9 | Hs.24756 | Tyrosine kinase substrate regulated by human growth factor | Double zinc finger motif, nucleotide binding site that can be induced by IL-2 stimulus |
| 10 | Hs.161137 | ESTs slightly similar to I38022 virtual protein | |
| 11 | Hs.348609 (Hs.125887) | Virtual protein FLJ 14464 | |
| 12 | Hs.24608 | DKFZP564D177 protein | Slightly similar to GBAS (protein containing signal peptide and transmembrane motif) |

Forty eight hours after the transfection, cells were once removed from the culture plate by trypsin treatment, and inoculated again on a 96-well culture plate at a cell density optimal for measurement. The trypsin treatment and the transfer of the cells on the 96-well culture plate were performed by a method widely used as a part of a cell culture method. The cells were further cultured overnight. Then, the medium containing 10% FBS was replaced with a medium containing 0.5% FBS and divided into two groups of plates, one of which was added with 100 ng/ml of TNFα. The cells were cultured at 37° C. in a $CO_2$ incubator for 4 hours. Then, both the plate containing TNFα and the plate containing no TNFα were washed with PBS, and the media were replaced. The cultures were added with a PBS solution containing 2% paraformaldehyde generally used for immobilizing cells and 10 ng/ml of a reagent for staining nuclei, Hoechst 33342 (Molecular Probes, Inc.), and the cells were immobilized at room temperature for 30 minutes.

Subsequently, the immobilization solution was washed away with PBS, and the cells were observed to examine whether the GFP fusion proteins had been transportred into the nuclei. For the observation, ArrayScan system manufactured by Cellomics was used. The ArrayScan system manufactured by Cellomics can confirm positions of nuclei based on staining using Hoechst 33342 and quantify the GFP amount in the recognized nuclei. This enables confirmation of whether GFP fusion proteins are transported into the nuclei by TNFα treatment.

The aforementioned 12 kinds of genes including unknown gene EST had been registered at the public database, but it was not known whether proteins encoded by these genes were transported into the nuclei by TNFα stimulus, and the relationship with TNFα and function of the genes were also unknown. Further, these genes included those estimated to be involved in the nuclear structure and included transcription factor-like motifs. Usefulness of the present invention was suggested by this study, which newly revealed their association with TNFα by the present invention.

Figure 6:
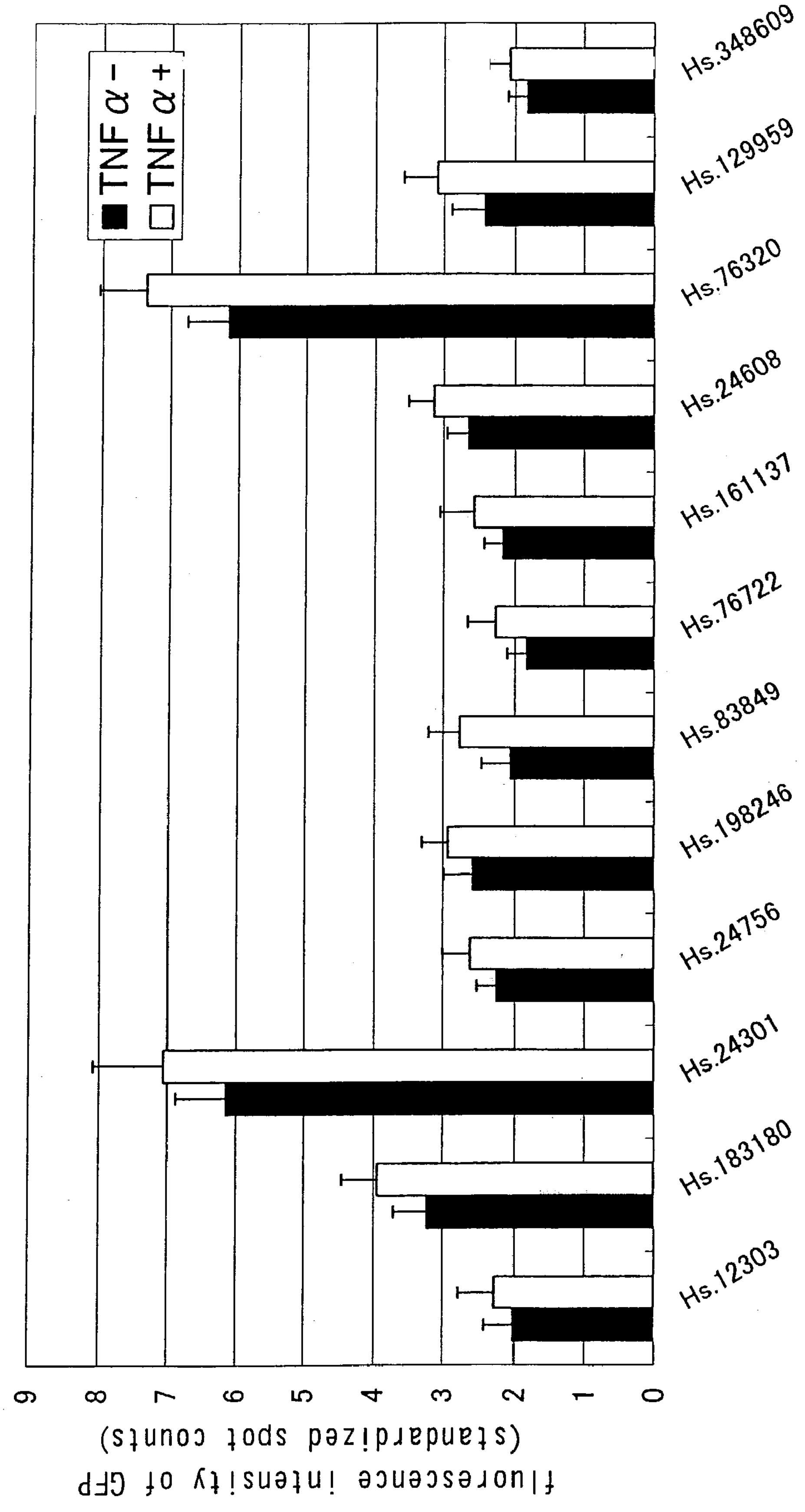
FIG. 6 shows nuclear transport in response to TNFα stimulus of proteins retrieved by the method of the present invention. The vertical axis represents fluorescence intensity of GFP.

Further, by using GFP protein alone, which is not a fusion protein, as a negative control of the experiment, it was confirmed that the GFP protein was not solely transported into the nuclei at all. However, as shown in FIG. 6, all the proteins encoded by the aforementioned 12 kinds of genes were transported into the nuclei by TNFα stimulus. FIG. 6 clearly shows that the GFP fluorescence was increased in the nuclei, and this indicates that fusion proteins distributed in the cytoplasm were transported into the nuclei by TNFα stimulus.

Thus, it was also confirmed by using another detector, that is, ArrayScan system, that the proteins encoded by the genes retrieved by the present invention were transported into the nuclei, and thus it was revealed that the genes isolated by the present invention surely coded for proteins transportred into the nucleus. Further, functions of the isolated genes were unknown, and it can be said that novel genes were found by the present invention, and thus usefulness of the present invention was demonstrated.

EXAMPLE 3

In Example 2, an example of searching for genes coding for proteins that are transported into nuclei in resposnse to TNFα stimulus was described. Described below is an example where genes coding for proteins that are transported into nuclei when cells are stimulated by applying heat shock to cells, that is, exposing cells to high temperature. Heat shock is a so-called burn model and cells ehibit various reactions to protect themselves. Therefore, it is considered that proteins that are transported into nuclei in response to heat shock also exist.

The cells used for this experiment were Chang Liver cells, namely, cells of an established cell line derived from human liver. For obtaining and culturing the cells, the same methods as in Examples 1 and 2 were used.

Vectors expressing fusion proteins of GFP and a cDNA library were transfected into cells in the same manner as in Examples 1 and 2. The cells were divided into two culture dishes and cultured in a $CO_2$ incubator at 37° C.

Twenty four hours after the transfection, one of the two culture dishes were transferred to a $CO_2$ incubator at 42° C. and left stand for 1 hour to apply heat shock to the cells, and then nuclei were isolated from the cells. The method for the isolation was according to the method described in "Labo Manual, Gene Engineering" (Maruzen). Cells in each culture dish were treated with trypsin so as to be removed from the dish and collected by centrifugation. The cells were washed with PBS and treated with 10 mM Tris-HCl (pH 7.4) containing 0.5% NP40, 10 mM NaCl and 3 mM $MgCl_2$ solution (NP40 lysis buffer) on ice for 10 minutes. The mixture was centrifuged again to precipitate cells, and the supernatant was replaced with a new NP40 lysis buffer to allow the cells to float. Then, centrifugation was performed again to collect nuclei as precipitates. The obtained nuclei were allowed to float in added PBS and then isolated by a cell sorter.

The operations thereafter including isolation of the nuclei, collection of plasmid DNA, transfection into *Escherichia coli* and sequence analysis of plasmid DNA were performed in the same manner as in Examples 1 and 2.

As a result of the experiment, 8 of new kinds of genes coding for proteins that are transported into the nuclei in response to heat, whose functions were unknown, were isolated from the cell group treated with heat shock.

As shown in the above examples, genes coding for proteins that are transported into nuclei in response to respective stimulus when cells are stimulated under various conditions could be efficiently retrieved by the present invention.

Industrial Applicability

According to the present invention, genes coding for proteins that are transported into nuclei in response to a certain stimulus can be cloned easily and reliably. Further, therapeutic agents for diseases caused by TNF stimulus can be screened.

What is claimed is:

1. A method for searching for a gene coding for a protein which is transported from cytoplasm into a nucleus through a nuclear pore in a eukaryotic cell, comprising the steps of:

(a) introducing a library of genes coding for fusion proteins of a marker protein whose localization in a cell can be detected and a part or whole of a search object protein into eukaryotic cells to allow expression of the genes in the transgenic cells so that the fusion proteins are produced, wherein one or more genes coding for a fusion protein autonomously transporting into the nucleus with no stimulus are eliminated from the library beforehand;

(b) dividing the transgenic cells into two groups and stimulating only cells of one group, wherein the stimulation transports a nuclear transport protein into nuclei of the cells, thereby transporting the fusion protein comprising a nuclear transport protein into nuclei of the cells;

(c) detecting localization of the fusion proteins in the cells by using the marker protein in each of the stimulated cell group and the unstimulated cell group and isolating cells in which the fusion proteins are localized in the nuclei or their nuclei; and (d) recovering genes coding for a fusion protein from the isolated cells or their nuclei, and comparing genes recovered from the stimulated cell group and genes recovered from the unstimulated cell group.

2. The method according to claim 1, comprising, after the step (d), a step of identifying a gene recovered only from the stimulated cell group or a gene recovered only from the unstimulated cell group.

3. The method according to claim 1, wherein, in the step (c), operations of detecting localization of the fusion proteins in a cell based on the marker protein and isolating cells or nuclei in which localization of the fusion proteins is observed in the nuclei are repeated twice or more for isolating cells or nuclei.

4. The method according to claim 1, wherein the marker protein is a protein emitting self-fluorescence, a protein catalyzing color development reaction, an antigen peptide that can be detected with an antibody or a peptide that can specifically bind to another substance.

5. The method according to claim 4, wherein the protein emitting self-fluorescence is a green fluorescent protein.

6. The method according to claim 1, wherein, in the step (b), the transport of the nuclear transport protein into the nuclei is stimulated by means selected from the group consisting of chemical substance, a physiologically active substance, environmental change and contact with other cells.

7. The method according to claim 1, wherein the cells or their nuclei are isolated by cell sorting, flow cytometry, microdissection or microscopic observation.

8. The method according to claim 1, wherein, in the step (c), permeability of the cell membranes is increased so that the fusion proteins in the cytoplasm should be flown out of the cells prior to the isolation of the cells.

9. The method according to claim 1, wherein, in the step (c), the cell membranes of the cells are disrupted and then the nuclei are isolated.

10. The method according to claim 1, wherein, in the step (d), the genes recovered from the stimulated cell group and the genes recovered from the unstimulated cell group are compared based on sequence analysis of full length or a part of a region coding for a search object protein for the genes.

11. The method according to claim 1, wherein, in the step (a), one or more genes coding for a fusion protein with an extranuclear protein, which is never transported into the nucleus, are eliminated from the gene library beforehand.

12. The method according to claim 1, wherein, in the step (a), the search object protein is a protein which regulates gene transcription.

13. The method according to claim 1, wherein, in the step (a), the fusion proteins further include a nuclear export signal.

* * * * *